(12) United States Patent
Fukuda et al.

(10) Patent No.: US 9,500,665 B2
(45) Date of Patent: Nov. 22, 2016

(54) SAMPLE PROCESSING APPARATUS AND AN ERROR DETECTING METHOD FOR SAMPLE PROCESSING APPARATUS

(71) Applicant: Sysmex Corporation, Kobe-shi, Hyogo (JP)

(72) Inventors: Masakazu Fukuda, Kobe (JP); Masamichi Tanaka, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 14/315,997

(22) Filed: Jun. 26, 2014

(65) Prior Publication Data

US 2015/0000428 A1   Jan. 1, 2015

(30) Foreign Application Priority Data

Jun. 27, 2013   (JP) ................................ 2013-135426

(51) Int. Cl.
*G01N 35/10*   (2006.01)
(52) U.S. Cl.
CPC ................ *G01N 35/1009* (2013.01)
(58) Field of Classification Search
None
See application file for complete search history.

(56) References Cited

U.S. PATENT DOCUMENTS

| | | | |
|---|---|---|---|
| 6,322,752 B1 * | 11/2001 | Siddiqui | G01N 35/10 422/105 |
| 6,370,942 B1 * | 4/2002 | Dunfee | G01N 35/1016 73/1.74 |
| 2001/0047692 A1 * | 12/2001 | Lipscomb | G01N 35/1009 73/864.25 |
| 2014/0190253 A1 * | 7/2014 | Nishida | G01N 35/1011 73/304 C |

FOREIGN PATENT DOCUMENTS

| | | |
|---|---|---|
| JP | 59-065769 A | 4/1984 |
| JP | 05-215755 A | 8/1993 |
| JP | 08-015273 A | 1/1996 |
| JP | 11-272324 A | 10/1999 |

* cited by examiner

*Primary Examiner* — Robert R Raevis
(74) *Attorney, Agent, or Firm* — Brinks Gilson & Lione

(57) ABSTRACT

A sample processing apparatus comprises an aspirating member which comprises a pump at one side and which is configured to aspirate a sample from the other side, a sensor which is configured to sense the presence or absence of a liquid at a predetermined position of the aspirating member, and a controller which is programmed to execute operations. The operations comprise controlling the aspirating member to aspirate a sample, obtaining a first sensing result by the sensor when the aspirating member aspirates a sample, controlling the aspirating member to aspirate air after aspirating a sample, obtaining a second sensing result by the sensor when the aspirating member aspirates air, and detecting an error in the aspirating operation, based on the first sensing result and the second sensing result.

20 Claims, 17 Drawing Sheets

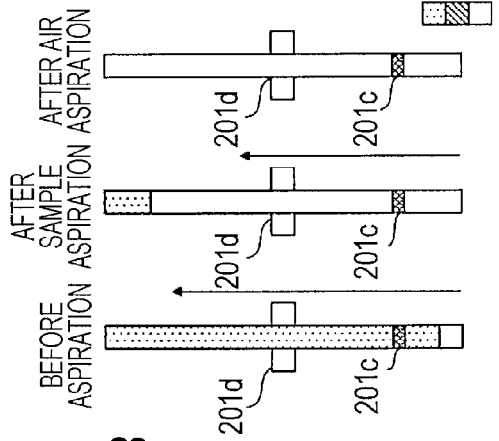
FIG. 6A
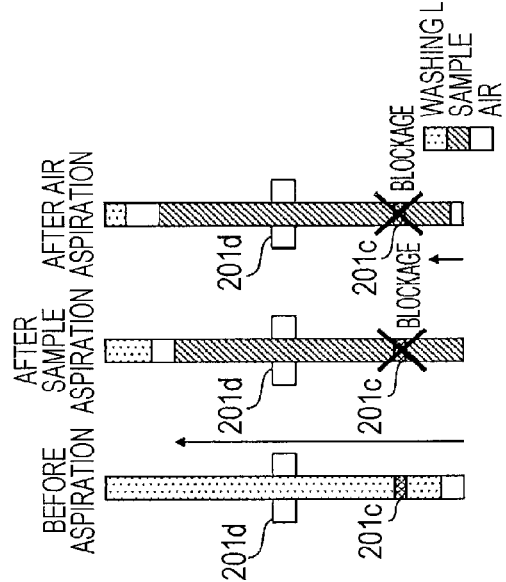
FIG. 6B
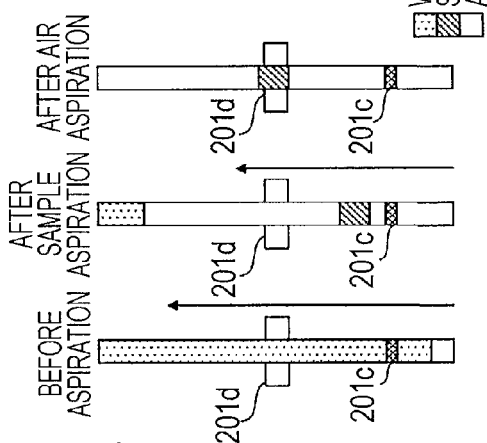
FIG. 6C
FIG. 6D

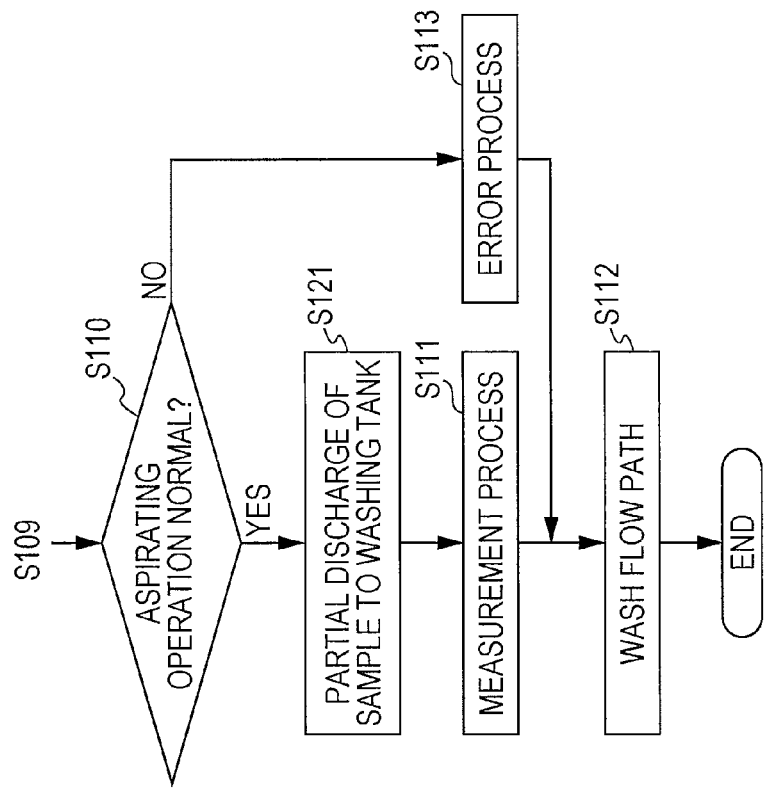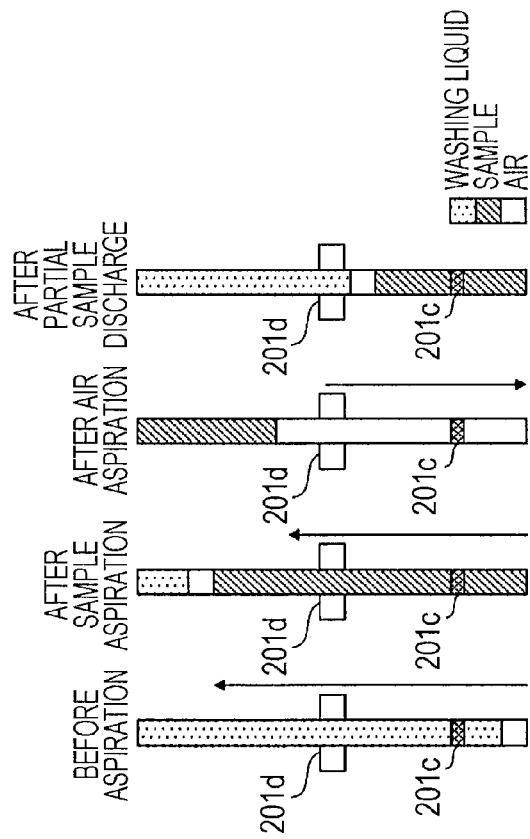

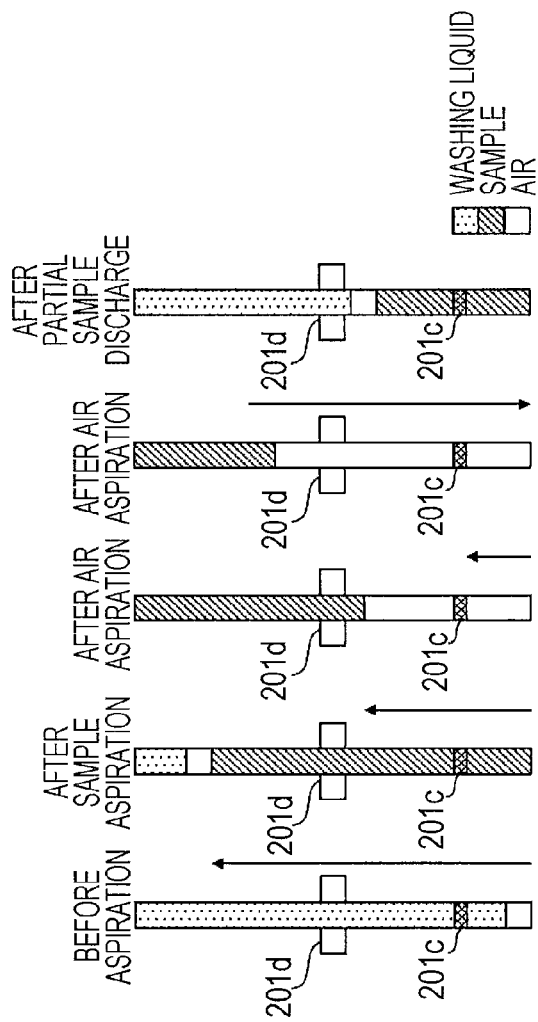

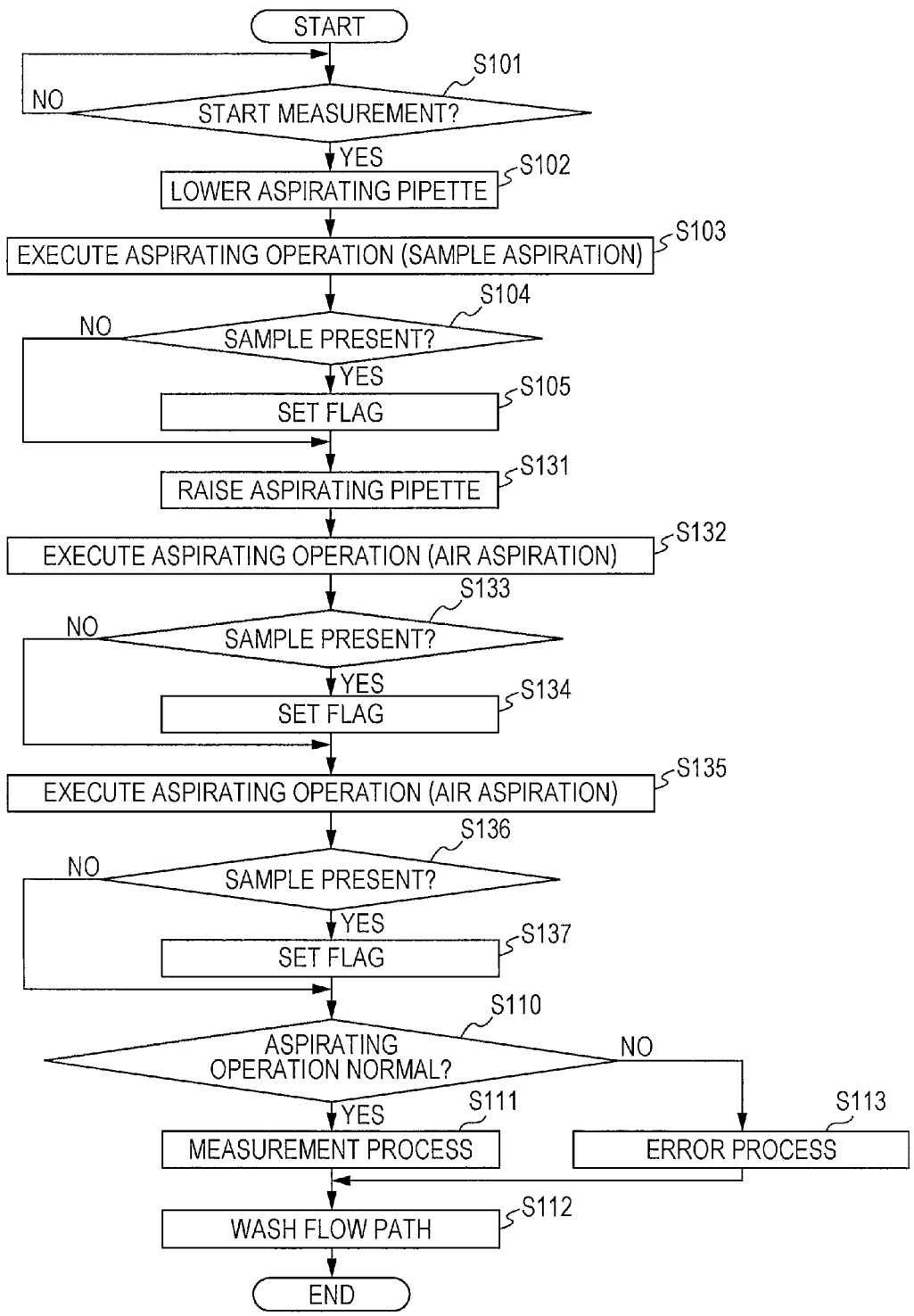

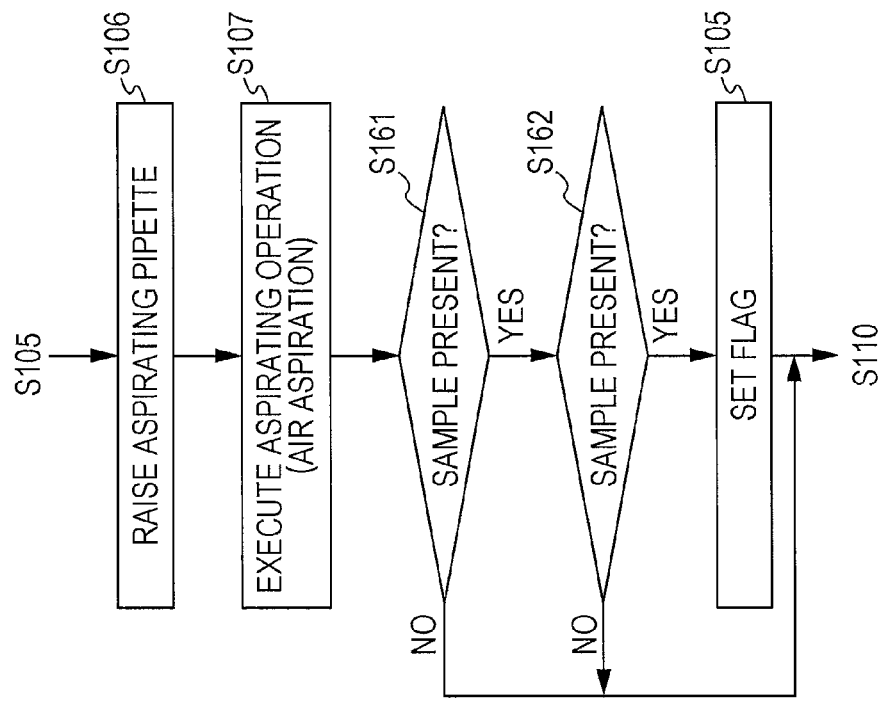
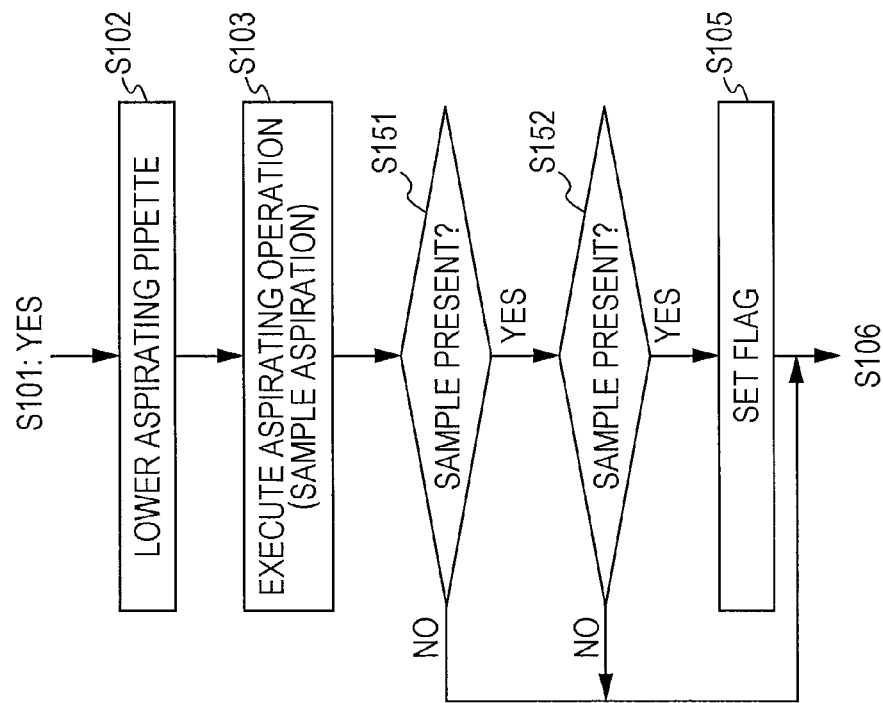

SAMPLE PROCESSING APPARATUS AND AN ERROR DETECTING METHOD FOR SAMPLE PROCESSING APPARATUS

RELATED APPLICATIONS

This application claims priority under 35 U.S.C. §119 to Japanese Patent Application No. 2013-135426 filed on Jun. 27, 2013 the entire content of which is hereby incorporated by reference.

FIELD OF THE INVENTION

The present invention relates to a sample processing apparatus for aspirating and processing a sample in a container, and an error detecting method for the sample processing apparatus.

BACKGROUND OF THE INVENTION

Sample processing apparatuses which perform processes such as measuring and analyzing sample such as blood and urine are provided with an aspirating unit to aspirate the sample from a container. A predetermined amount of the sample aspirated from one end of the aspirating unit is mixed with reagent such as diluting liquid, drug or the like for processing. Thereafter, the aspirating unit is washed with a washing liquid.

Methods of collecting and quantifying a predetermined amount of aspirated sample include types wherein a predetermined amount of sample is aspirated from one end of an aspirating unit and dispensed into a chamber (for example, Japanese Laid-Open Patent Application No. 1111-272324), and types wherein sample is quantified and collected by a sampling valve provided in the aspirating unit and flows to a chamber together with reagent (for example, Japanese Laid-Open Patent Application No. S59-65769).

When sample is collected via these methods, there is a possibility of adverse effect in the processing results when sample is not properly aspirated by the aspirating unit. To prevent such a problem, a sensor is provided in the aspirating unit to monitor the status of the aspiration performed by the aspirating unit. For example, in the apparatus disclosed in Japanese Laid-Open Patent Application No. H08-015273, an optical detect device is provided in the middle part of the sample flow path to detect clogging of the sample needle by detecting the length of the air column aspirated in the sample flow path via the optical detecting device.

The method disclosed in Japanese Laid-Open Patent Application No. H08-015273 specifically detects an error in the aspiration operation due to clogging of the sample needle and cannot handle the detection of other errors in the aspiration operation.

SUMMARY OF THE INVENTION

The scope of the present invention is defined solely by the appended claims, and is not affected to any degree by the statements within this summary.

A first aspect of the present invention is a sample processing apparatus comprising an aspirating member which comprises a pump at one side and which is configured to aspirate a sample from the other side, a sensor which is configured to sense the presence or absence of a liquid at a predetermined position of the aspirating member, and a controller which is programmed to execute operations. The operations comprise controlling the aspirating member to aspirate a sample, obtaining a first sensing result by the sensor when the aspirating member aspirates a sample, controlling the aspirating member to aspirate air after aspirating a sample, obtaining a second sensing result by the sensor when the aspirating member aspirates air, and detecting an error in the aspirating operation, based on the first sensing result and the second sensing result.

A second aspect of the present invention is an error detecting method for a sample processing apparatus, comprising aspirating sample from a container through an aspirating member which has a sensor capable of detecting a liquid, obtaining a first sensing result by the sensor when the aspirating member aspirates a sample, aspirating air through the aspirating member after the sample is aspirated, obtaining a second sensing result by the sensor when the aspirating member aspirates air, detecting an error in the aspirating operation, based on the first sensing result and the second sensing result.

BRIEF DESCRIPTION OF THE DRAWINGS

FIGS. 6A-6D schematically show the condition of the flow path peripheral to the liquid detecting unit during an abnormal sample liquid aspirating operation of the embodiment;

FIGS. 11A and 11B schematically show the condition of the flow path peripheral to the liquid detecting unit during the normal sample liquid aspirating operation of the first modification;

FIGS. 13A and 13B schematically show the condition of the flow path peripheral to the liquid detecting unit during the normal sample liquid aspirating operation of the second modification;

FIG. 14 is a flow chart showing the control during the measurement operation of the second modification.

FIGS. 16A and 16B are flow charts showing the control during the measurement operation of a fourth modification.

DETAILED DESCRIPTION OF THE PREFERRED EMBODIMENTS

Figure 1:
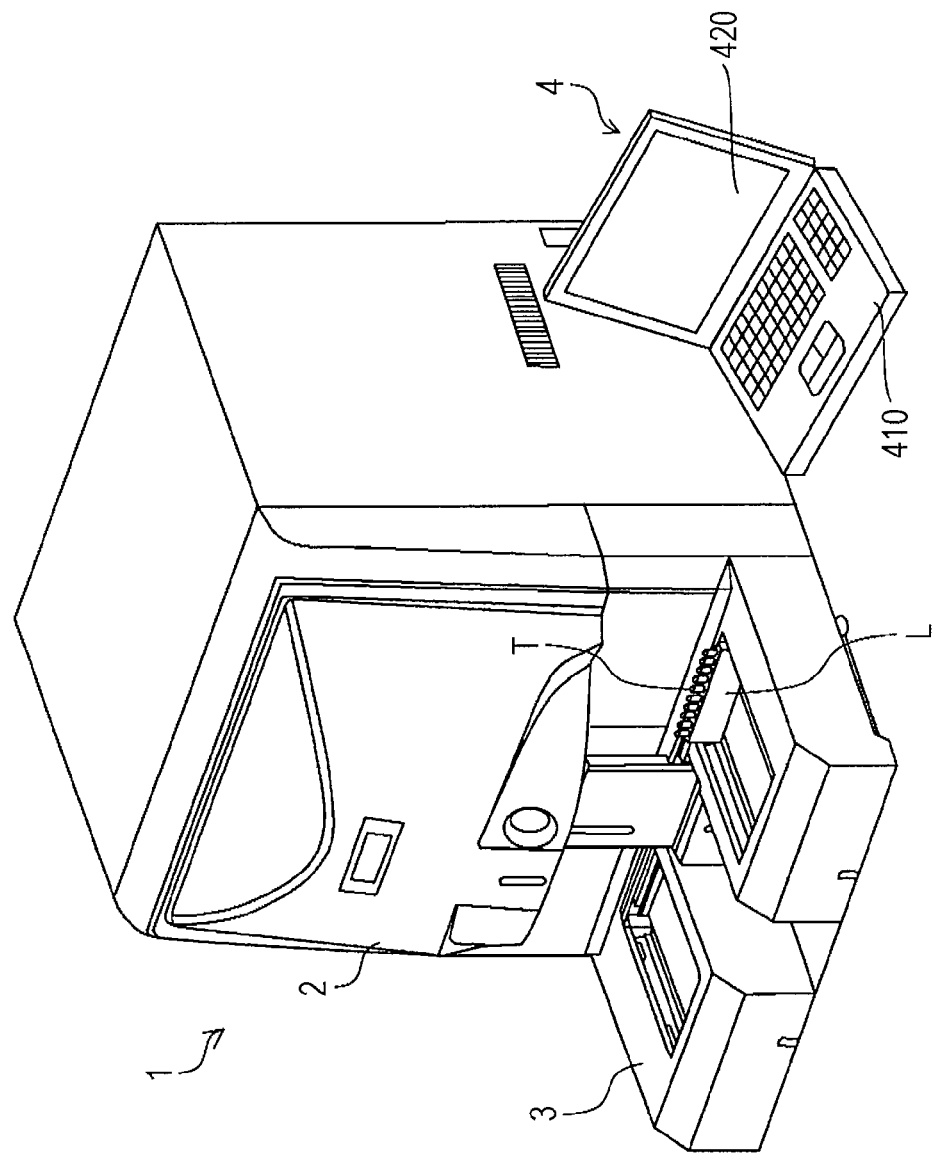
FIG. 1 shows the structure of the urine analyzer of the embodiment.

The preferred embodiments of the present invention will be described hereinafter with reference to the drawings.

The present embodiment applies the invention to a urine analyzer which performs multilevel aspiration operations on a urine sample, and detects error in the aspirating unit obtained from the results of the aspirating operations.

The urine analyzer of the embodiment is described below referring to the drawings.

FIG. 1 shows the structure of the urine analyzer 1 of the present embodiment.

The urine analyzer 1 has a measuring device 2, transporting device 3, and information processing device 4. The measuring device 2 is configured to optically measure via flow cytometer the solid components in urine such as bacteria and white blood cells typically contained in urine samples. The transporting device 3 transports the sample rack L to supply the sample container T to the measuring device 2. The information processing device 4 analyzes the measurement results obtained from the measuring device 2, and displays the analysis results on the display unit 420.

Figure 2:
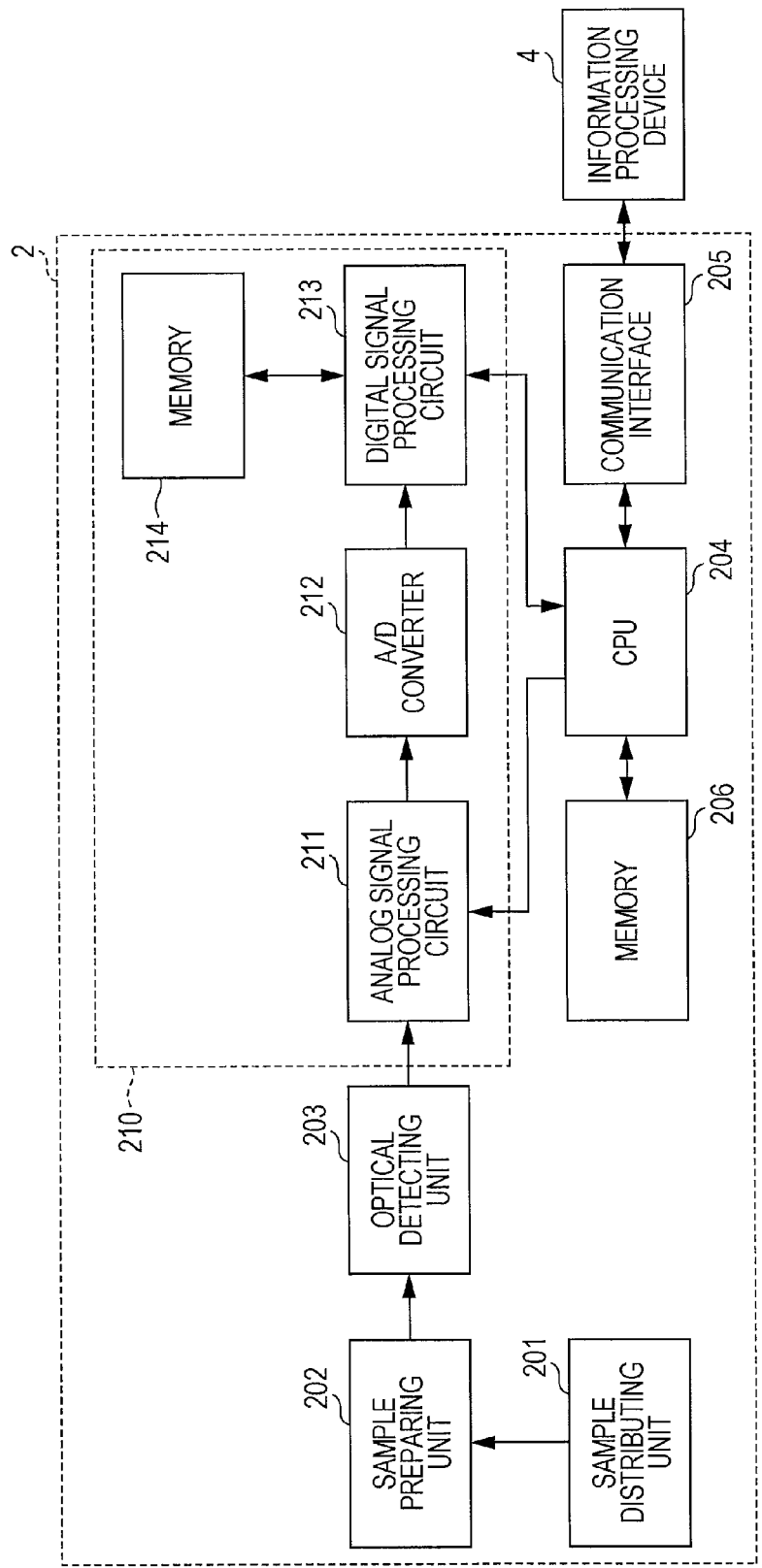
FIG. 2 shows the structure of the measuring device of the embodiment.

FIG. 2 is a block diagram showing the structure of the main part of the measuring device 2.

The measuring device 2 includes a sample distributing unit 201, sample preparing unit 202, optical detecting unit 203, signal processing unit 210, CPU 204, communication interface 205, and memory 206. The signal processing unit 210 has an analog signal processing circuit 211, A/D converter 212, digital signal processing circuit 213, and memory 214.

The sample distributing unit 201 is provided with an aspirating pipette and pump. The sample distributing unit 201 is further provided with a predetermined drive mechanism to drive the aspirating pipette. The sample distributing unit 201 aspirates a predetermined amount of sample from a sample container T supplied by the transporting device 3 by driving the pump while the aspirating pipette is in the lowered state. After aspirating the sample, the sample distributing unit 201 pump is driven while the aspirating pipette is in the raised state, then air is aspirated.

In the present embodiment, the presence or absence of an error in the aspirating operation is determined by combining the sample liquid aspirating operation and the air aspirating operation as described above. When the aspirating operation is determined to be error free, the sample distributing unit 201 supplies the sample aspirated into the aspirating pipette to the sample preparing unit 202. Note that the process of determining the presence or absence of an error in the aspirating operation when a sample aspirating operation is performed is described below with reference to FIGS. 5A through 8C.

The sample preparing unit 202 includes reagent containers, mixing containers, pump and the like. The sample supplied from the sample distributing unit into the mixing container is mixed with diluting liquid and stain from the reagent containers to prepare the measurement sample. The measurement sample prepared in the mixing container is supplied together with sheath fluid to a sheath flow cell 203a of the optical detecting unit 203.

The optical detecting unit 203 irradiates laser light on the measurement sample, and outputs electrical signals based on the produced forward scattered light, side fluorescent light, and side scattered light to the analog signal processing circuit 211. The optical detecting unit 203 is provided with an irradiating optical system to irradiate laser light on a measurement sample flowing through the sheath flow cell 203a, and a light receiving optical system to receive the produced forward scattered light, side fluorescent light, and side scattered light. The structure of such optical systems is well known, hence, detailed description is omitted.

The analog signal processing circuit 211 amplifies and outputs electrical signals received from the optical detecting unit 203 to the A/D converter 212 according to the instructions of the CPU 204. The A/D converter 212 converts the electrical signals amplified by the analog signal processing circuit 211 to digital signals, which are then output to the digital signal processing circuit 213. The digital signal processing circuit 213 performs predetermined signal processing of the digital signals received from the A/D converter 212 according to the instructions of the CPU 204. The processed digital signals are then stored in the memory 214.

The CPU 204 receives the control signals from the information processing apparatus 4 through the communication interface 205, and controls each part of the measuring device 2 according to these control signals. The CPU 204 generates measurement data based on the forward scattered light and side fluorescent light from the digital signals stored in the memory 214, and outputs the measurement data to the communication interface 205. The CPU 204 also transmits the detection results of a liquid sensor unit (described later, refer to FIG. 3) through the communication interface 205 to the information processing device 4.

The communication interface 205 transmits the measurement data output from the CPU 204 to the information processing device 4, and receives control signals output from the information processing device 204. The memory 206 is used as the work area of the CPU 204.

Figure 3:
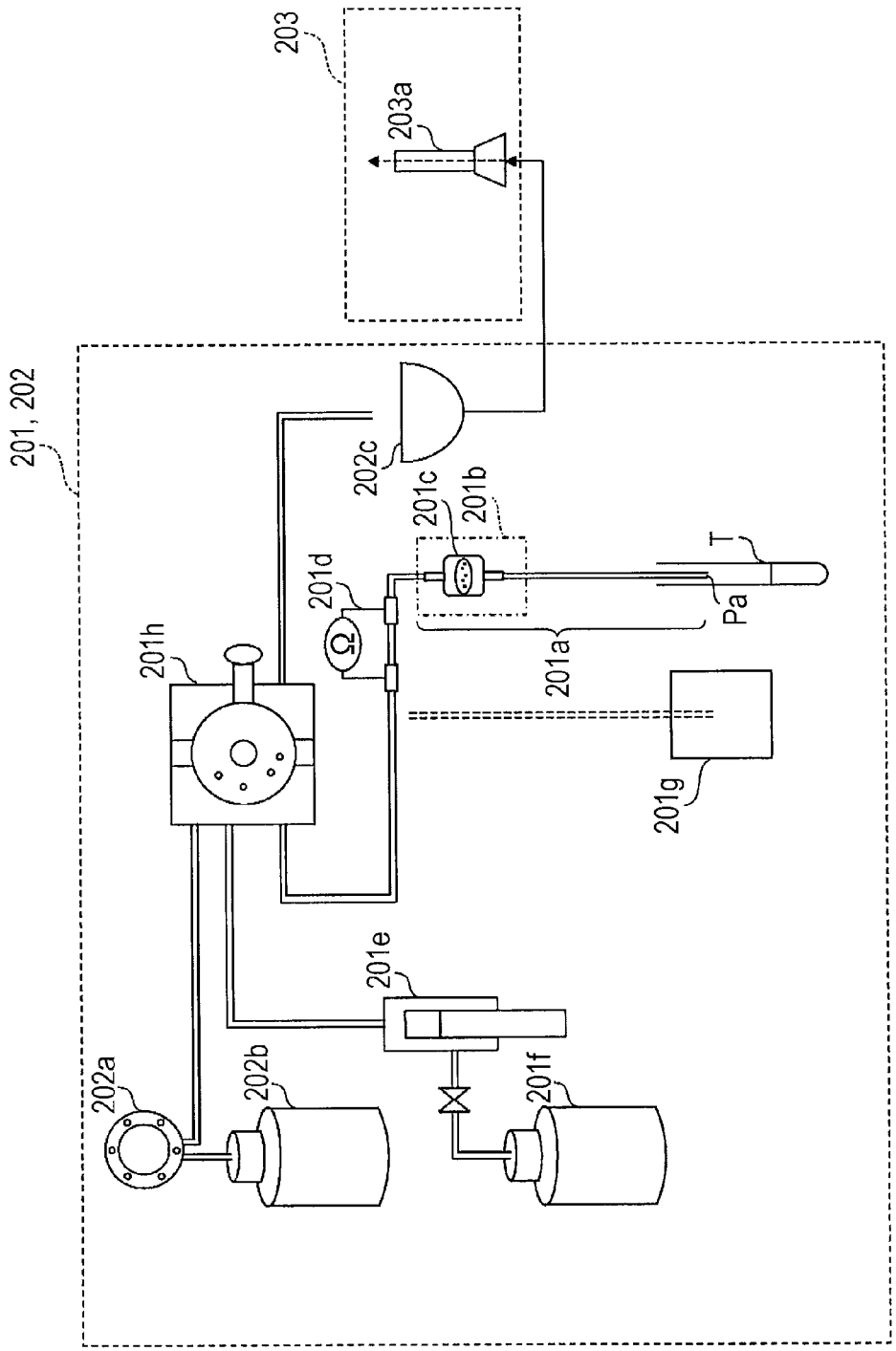
FIG. 3 shows the structures of the sample distributing unit and the sample preparing unit of the embodiment.

FIG. 3 briefly shows the structures of the sample distributing unit 201 and the sample preparing unit 202. Note that FIG. 3 shows the flow path and drive mechanisms from the aspirating pipette 201a to the reaction chamber 202 in the sample distributing unit 201 and the sample preparing unit 202, and other flow paths and drive mechanisms are omitted.

Referring to FIG. 3, the sample distributing unit 201 is provided with an aspirating pipette 201a, lifting device 201b, sample filter 201c, liquid sensing unit 201d, syringe pump 201e, washing liquid container 201f, washing tank 201g, and sampling valve 201h. The sample preparing unit 202 has a diaphragm pump 202a, diluting liquid container 202b, and reaction chamber 202c. The aspirating pipette 201a and the syringe pump 201e are connected by a resin tube which functions as an aspiration line. The device for aspirating sample liquid (urine) held in the sample container T includes the aspirating pipette 201a, syringe pump 201e, and aspiration line, and is referred to as the "aspirating unit." The side of the aspirating port Pa is referred to as the upstream side of the aspirating unit, and the side of the syringe pump 201e is referred to as the downstream side of the aspirating unit.

In the sample aspirating operation, the aspirating pipette 201a is lowered by the lifting device 201b and inserted in the sample container T. Hence, the aspirating port Pa provided at the end of the aspirating pipette 201a is immersed in the sample liquid held in the sample container T. In this condition, a negative pressure is induced in the aspirating pipette 201a by the syringe pump 201e. Sample liquid is thus aspirated. The aspirated sample passes through the interior of the aspirating pipette 201a and is delivered to the sampling valve 201h via the sampling valve 201c and the liquid sensing unit 201d. Thereafter, the aspirating pipette 201a is lifted by the lifting device 201b so that the aspirating port Pa is separated from the liquid surface of the sample held in the sample container T. In this condition, a negative pressure is induced in the aspirating pipette 201a by the syringe pump 201e, and air is aspirated by the aspirating pipette 201a.

The sample filter 201c has a plurality of small pores to remove the unwanted substances in the aspirated sample.

The liquid sensing unit 201d is configured by two electrodes, and a detecting circuit to detect changes in voltage between the electrodes. The liquid sensing unit 201d is disposed in the aspiration line connecting the aspirating pipette 201a and the syringe pump 201e. When an electrolytic sample liquid flows between the electrodes, the current flows to the sample between the electrodes and the voltage changes between the electrodes. The detecting circuit of the liquid sensing unit 201d outputs detection signals to the CPU 204 of the measuring device 2 when the amount of voltage fluctuation exceeds a predetermined threshold value. That is, when a sample liquid is present between the electrodes, the detection signals indicating the presence of the sample are output from the liquid sensing unit 201d to the CPU 204.

The sampling valve 201h measures the aspirated sample by the operation of a switching arm. The quantified sample is dispensed to the reaction chamber 202c together with diluting liquid from the diluting liquid container 202b. Stain from the stain container is also dispensed to the reaction chamber 202c to stain the sample via the colorant contained in the stain.

The prepared sample is delivered to the optical detecting unit 203, forming a narrow flow encapsulated in sheath fluid within the sheath flow cell 203a, and irradiated by laser light. This operation is performed automatically by operating the drive units and electromagnetic valves (not shown in the drawing) via the control of the information processing device 4.

When the measurement of the sample is completed, a flow path washing operation is performed. The aspirating pipette 201a is first moved to the washing tank 201g by predetermined drive device (not shown in the drawing). The switching arm of the sampling valve 201h is switched to a position in the flow path between the aspirating pipette 201a and the syringe pump 201e. Thereafter, a negative pressure is induced in the flow path from the syringe pump 201e, and the electromagnetic valve of the washing liquid container 201f is opened. The washing liquid within the washing liquid container 201f is therefore discharged into the washing tank 201g through the syringe pump 201e, sampling valve 201h, and the aspirating pipette 201a. Hence, the sample aspiration flow path is washed. The exterior of the aspirating pipette 201a is also washed by the discharge of the washing liquid from the aspirating pipette 201a in the washing liquid tank 201g. Note that the other flow path devices, such as the reaction chamber 202c, are washed by predetermined washing devices which are not shown in the drawing.

When the washing of the aspirating pipette 201a is completed, the aspirating pipette 201a is returned to the initial position to allow aspiration of the sample liquid for the next measurement operation. With the aspirating pipette 201a in the raised position, a negative pressure is applied to the aspirating pipette 201a by the syringe pump 201e, and a small amount of air is aspirated from the aspirating pipette 201a. Hence, an air layer is produced between the washing liquid filling the aspirating pipette 201a and the sample liquid to be aspirated for the next measurement, thereby preventing any mixing of the washing liquid and the sample. Note that in the present embodiment the amount of drawn air is regulated to form an extremely small air layer so as to have a substantially constant aspiration speed of the next sample.

Figure 4:
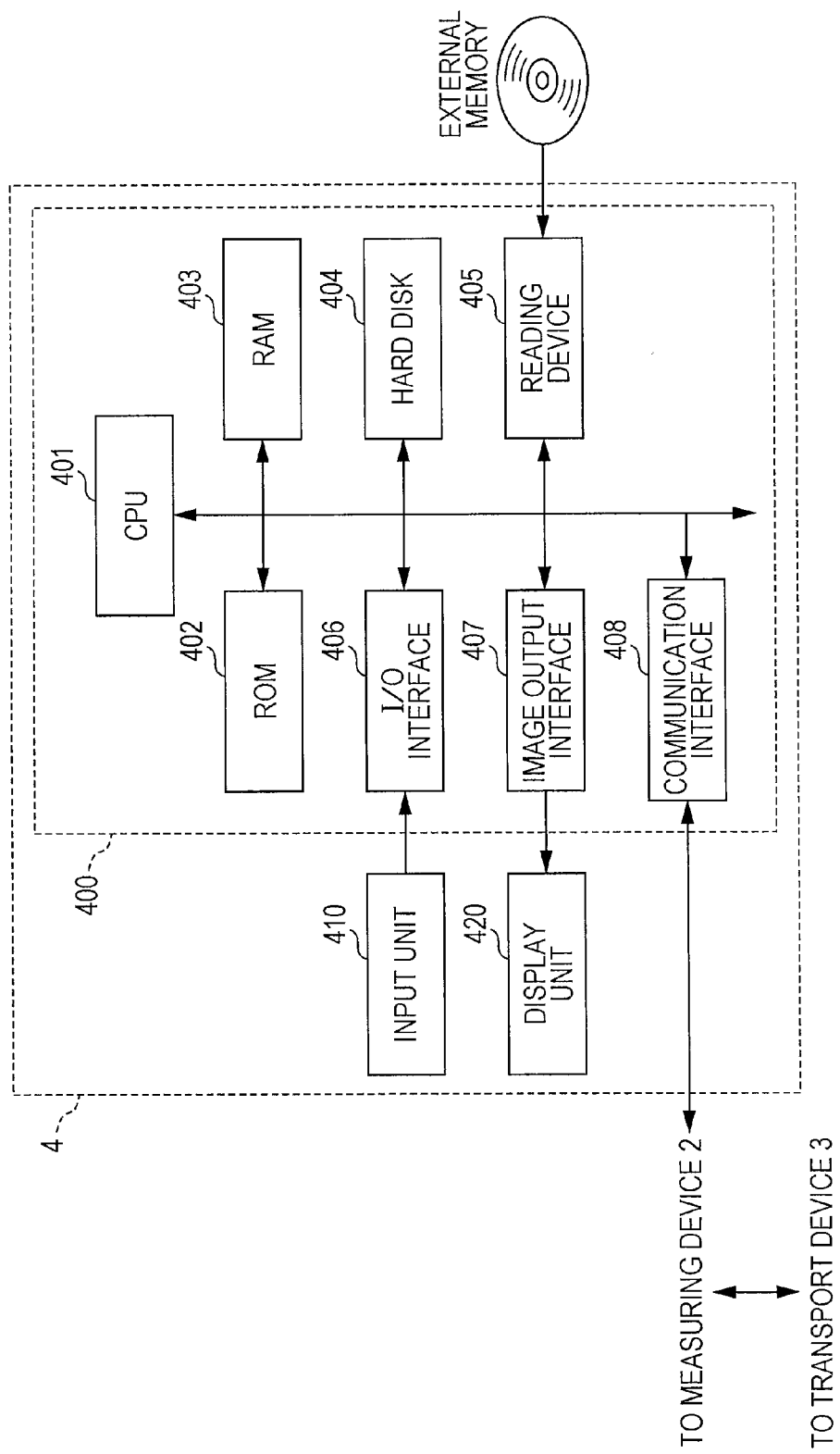
FIG. 4 shows the structure of the information processing device of the embodiment.

FIG. 4 shows the structure of the information processing device 4.

The information processing device 4 is configured by a personal computer having a main body 400, input section 410, and display 420. The main body 400 has a CPU 401, ROM 402, RAM 403, hard disk 404, reading device 405, I/O interface 406, image output interface 407, and communication interface 408.

The CPU 401 is capable of executing a computer program stored in the ROM 402 and a computer program loaded in the RAM 403. The RAM 403 is used when reading the computer programs stored in the ROM 402 and recorded on the hard disk 404. The RAM 403 is also used as the work area of the CPU 401 when the CPU 401 executes the computer programs.

An operating system and application programs, as well as the data used when executing the operating system and application programs that are executed by the CPU 401, are installed on the hard disk 404. Measurement data received from the measuring device 2 are also stored on the hard disk 404.

Programs for analyzing samples based on measurement data, and display programs for displaying analysis results on the display unit 420 are also installed on the hard disk 404. Analysis process and display process are performed by installing the aforesaid programs. That is, the CPU 401 performs the functions of executing the processes shown in FIG. 7 (to be described later), and further functions of displaying the screens shown in FIGS. 8A through 8C via the above programs.

The reader 405 is configured by a CD drive or DVD drive capable of reading computer programs and data recorded on an external storage such as a recording medium. Hence, the programs executed by the information processing device 4 can be updated through an external storage such as a recording medium.

The I/O interface 406 is connected to the input section 410 configured by a mouse and keyboard, and the user uses the input section 410 to input data to the information processing device 4. The image output interface 407 is connected to the display section 420 configured by a display of some type, and the image output interface 407 outputs image signals corresponding to the image data to the display unit 420. The display unit 420 displays images based on the input image signals.

Measurement data transmitted from the measuring device 2 can be received by the communication interface 408. The measurement data are stored on the hard disk 404.

The sample aspirating operation and error determining process of the aspirating operation of the urine analyzer 1 of the present embodiment are described below.

Figure 5B:
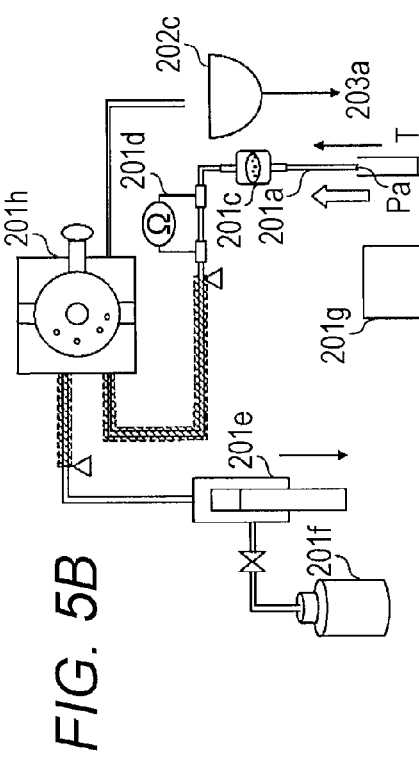
FIGS. 5A-5D schematically show the normal sample liquid aspirating operation of the embodiment.
Figure 5D:
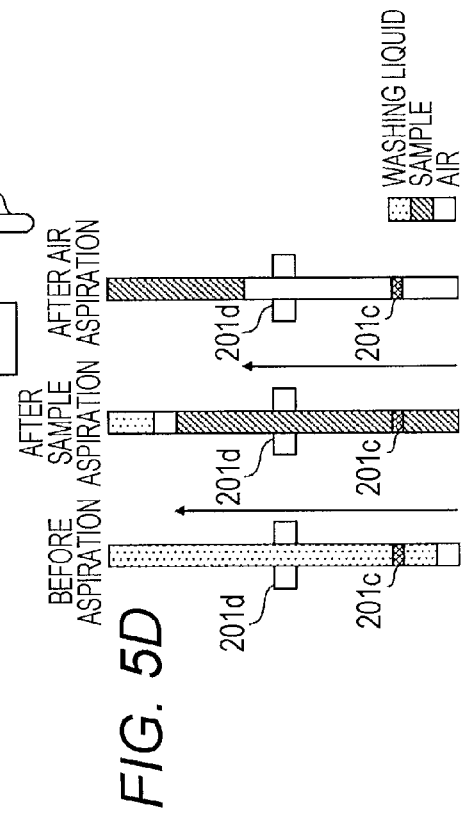
Figure 5A:
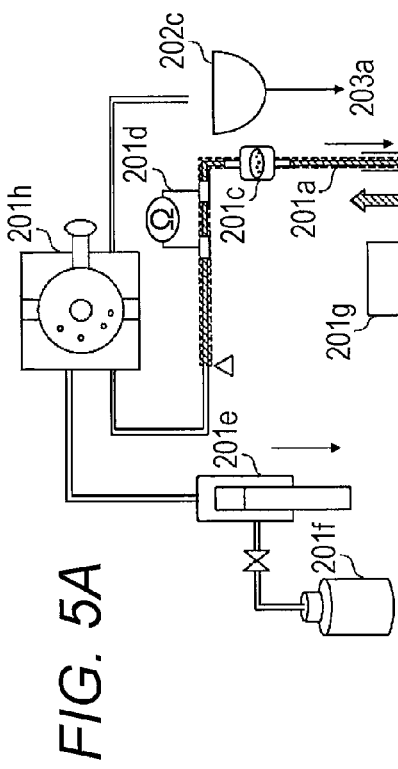
Figure 5C:
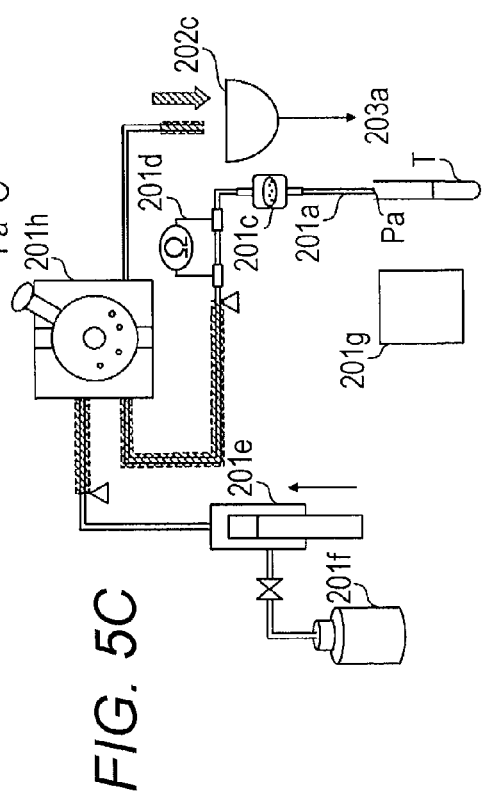

FIGS. 5A through 5C schematically show the normal sample liquid aspirating operation. FIG. 5D schematically shows the condition of the flow path on the periphery of the liquid sensing unit 201d during a normal sample aspirating operation. Note that only the flow paths used in sample aspiration are shown in FIGS. 5A through 5C. Although the end part of the aspirating pipette 201a is the end part of the flow path in FIG. 5D, the drawing of the pipette 201a is omitted.

In the condition prior to aspirating the sample, washing liquid fills the flow path from the liquid sensing unit 201d to the sampling valve 201c by the washing operation of the previous measuring operation, as shown at the side of FIG. 5D. An air layer is also provided at the end of the flow path. Note that the symbol [Δ] in the drawing is shown at both ends of the sample liquid.

Referring to FIG. 5A, during sample aspiration the aspirating pipette 201a is first lowered so that the aspiration port Pa of the aspirating pipette 201a is submerged in the sample liquid held in the sample container T. In this condition a negative pressure is induced by the syringe pump 201e to aspirate the sample. The sample is thereby moved through the sampling valve 201c to the downstream side of the aspirating unit. In the first aspirating operation, the sample is positioned so that the front end of the sampling liquid is at a position exceeding the position of the electrodes of the liquid sensing unit 201d. Thus, the condition shown in the center part of FIG. 5D is achieved. In this condition the sample liquid is detected by the liquid sensing unit 201d because the sample is interposed between the electrodes of the sample sensing unit 201d.

As shown in FIG. 5D, the aspirating pipette 201a is then raised so that the aspiration port Pa is separated from the surface of the sample liquid held in the sample container T. In this condition a negative pressure is induced by the syringe pump 201e to aspirate air. The sample previously aspirated in the first aspirating operation is thereby moved to the downstream side of the aspirating unit. In the second aspirating operation, the sample is positioned so that the back end of the sampling liquid is at a position exceeding the position of the electrodes of the liquid sensing unit 201d. Thus, the condition shown at the right end of FIG. 5D is achieved. In this condition the sample liquid is not detected by the liquid sensing unit 201d because air is interposed between the electrodes of the sample sensing unit 201d.

As shown in FIG. 5C, the sampling valve 201h is then operated to dispense the measured sample into the reaction chamber 202c.

When the aspirating operation is performed normally in the present embodiment, the amount of aspirated sample and air and the length of the flow path are adjusted so that the sample is detected by the liquid sensing unit 201d in the first aspirating operation, and the sample is not detected by the liquid sensing unit 201d in the second aspirating operation. Whether an error occurs in the aspirating operations can be determined, as described below, via this configuration based on the detection results indicating the presence and absence of sample during the two aspirating operations.

In this embodiment, the amount of sample aspirated from the sample container T is controlled by suctioning air in the second aspirating operation. For example, when only the sample liquid is aspirated in a single aspiration operation and the sample reaches the sampling valve 201h, the sample must be aspirated in sufficient quantity to fill the length of the aspiration line up to the sampling valve 201h. Conversely, sample can be supplied to the sampling valve 201h while minimizing the amount of aspirated sample because air is aspirated in a second operation in the present embodiment. Thus, aspirating unnecessary sample is avoided. Furthermore, the amount of sample passing through the sampling valve 201c is reduced because the amount of aspirated sample is decreased, and as a result clogging of the sampling valve 201c is also suppressed.

An example of an error in the aspirating operation is described below.

FIGS. 6A through 6C schematically show the condition of the flow path on the periphery of the liquid sensing unit 201d during a normal sample aspirating operation. FIG. 6D shows an example of the determination method of the sample aspirating operation. In FIG. 6D, the symbol [○] indicates sample is detected by the liquid sensing unit 201d, and the symbol [X] indicates sample is not detected by the liquid sensing unit 201d.

In the case of urine collected from a patient suffering from urinary tract infection, for example, the sample will contain many impurities, or have large particle components such as aggregated leukocytes. In this case, the impurities and particle components are captured by the sample filter 201c, which results in clogging of the sample filter 201c. The aspiration of sample which is comparatively problem free at the beginning of the aspirating operation gradually progresses at reduced aspirating speed until the flow of sample halts in the aspirating unit.

In this case, sample is detected by the liquid sensing unit 201d during the first sample aspirating operation (sample aspiration), and later sample is also detected by the liquid sensing unit 201d during the second liquid aspirating operation (air aspiration, as shown in FIG. 6A. In the second aspirating operation, air does not reach the position between the electrodes of the liquid sensing unit 201d since the aspiration of sample is halted by the clogging of the sample filter 201c. In the present embodiment, when sample liquid is detected during both the first and second aspiration operations, the determination is that the sample filter 201c is blocked as shown in FIG. 6D.

A further example pertains to starting the sample aspirating operation when the sample container T does not contain sample, whereby only air is aspirated and sample liquid is not aspirated when the aspirating pipette 201a is in the lowered condition.

In this case, sample is not detected by the liquid sensing unit 201d in neither the first or the second aspiration operation as shown in FIG. 6B. In the present embodiment, when sample liquid is not detected during neither the first or second aspiration operations, the determination is that the sample container T does not contain sample as shown in FIG. 6D.

Note that other than when absolutely no sample is held in the sample container T, the presence of a slight amount of sample, that is, an amount insufficient for aspiration by the aspirating pipette 201a, results in the same detection as when there is no sample in the sample container T by the liquid sensing unit 201d. Therefore, the determination that there is no sample in the sample container T is also made in this case.

If for some reason the sample is not detected by the liquid sensing unit 201d during the first aspirating operation, the sample may be detected by the liquid sensing unit 201d during the second aspirating operation. For example, if sample is not aspirated during the first aspirating operation sample adhered to the inner wall of the aspirating unit may collect and migrate to the position of the liquid sensing unit 201d.

In this case, the sample is not detected in the first aspirating operation, and the sample is detected in the second aspirating operation, as shown in FIG. 6C. In the present embodiment, when the sample is not detected in the first aspirating operation but the sample is detected in the second aspirating operation, it is determined that the sample aspirating operation was improper for some reason.

Figure 7:
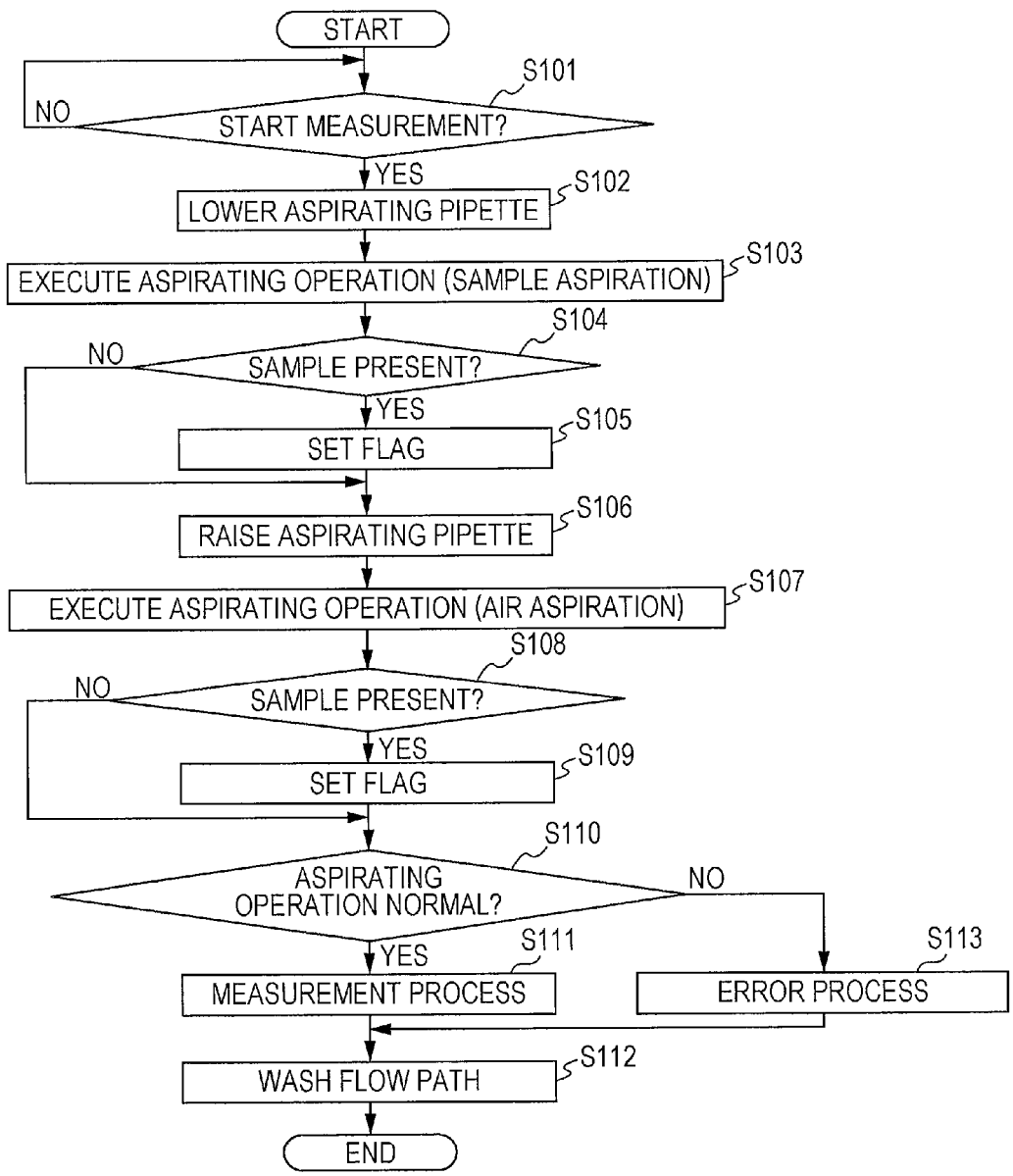
FIG. 7 is a flow chart showing the control during the measurement operation of the embodiment.

FIG. 7 is a flow chart showing the control during the measurement operation. The control is executed by the CPU 401 of the information processing device 4. The control in FIG. 7 is performed for each sample container T held in the sample rack L.

Referring to FIG. 7, the CPU 401 of the information processing device 4 waits for the sample container T holding the sample to be measured is delivered to the aspirating position (S101). When the sample container T containing the sample to be measured is moved to the aspirating position (S101: YES), the CPU 401 lowers the aspirating pipette 201a to near the bottom of the sample container T (S102), and executes the first aspirating operation of the measuring unit 2 (S103). When the first aspirating operation is completed, the CPU 401 determines whether sample is detected by the liquid sensing unit 201d (S104). When the sample has been detected by the liquid sensing unit 201d (S104: YES), the CPU 401 stores the flag information indicating that sample has been detected in the first aspirating operation in the RAM 403 (S105). When sample is not detected by the liquid sensing unit 201d (S104: NO), the CPU 401 advances the process to S106. This completes the first aspirating operation.

The CPU 401 then lifts the aspirating pipette 201a to a positioned at which the aspiration port Pa of the aspirating pipette 201a is separated from the surface of the sample liquid (S106). In this condition the CPU 401 executes the second aspirating operation of the measuring device 2 (S107). When the second aspirating operation is completed, the CPU 401 determines whether sample is detected by the liquid sensing unit 201d (S108). When the sample has been detected by the liquid sensing unit 201d (S108: YES), the CPU 401 stores the flag information indicating that sample has been detected in the second aspirating operation in the RAM 403 (S109). When sample is not detected by the liquid sensing unit 201d (S108: NO), the CPU 401 advances the process to S110. This completes the second aspirating operation.

The CPU 401 then references the flag information stored in the RAM 403, and determines whether the sample aspirating operations were normal via the method shown in FIG. 6D (S110). Specifically, when the sample is detected in the first aspirating operation and the sample is not detected in the second aspirating operation, the CPU 401 determines that the aspirating operations are normal, and advances the process to S111. When the sample is detected in the first aspirating operation and the sample is also detected in the second aspirating operation, the CPU 401 determines that the sample filter 201c is blocked, and the process advances to S113. When the sample is not detected in the first aspirating operation and the sample is also not detected in the second aspirating operation, the CPU 401 determines that there is no sample in the sample container T, and the process advances to S113. When the sample is not detected in the first aspirating operation but the sample is detected in the second aspirating operation, the CPU 401 determines that the sample aspirating operation proper for some reason, and the process advances to S113.

When the aspirating operations are determined normal (S110: YES), the CPU 401 measures the amount of the aspirated sample via the sampling valve 201h, discharges the measured amount of sample to the reaction chamber 202c, and performs the measuring process on the sample. When the measuring process is completed, the CPU 401 washes the flow path as previously described (S112). Alternatively, when the aspirating operations are determined abnormal (S110: NO), the CPU 401 executes the error process for the abnormal container (S113).

Figure 8A:
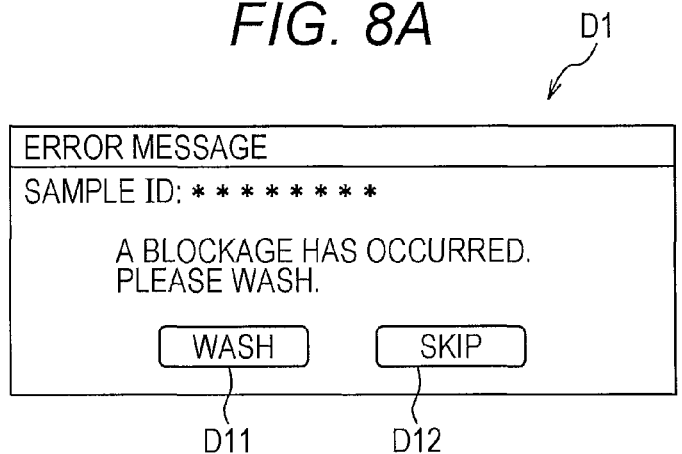
FIGS. 8A-8C show examples of the screen displayed on the display unit of the information processing apparatus in the error process of the embodiment.
Figure 8B:
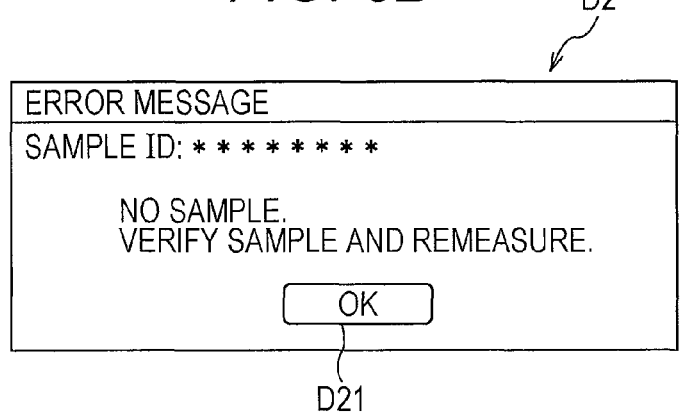
Figure 8C:
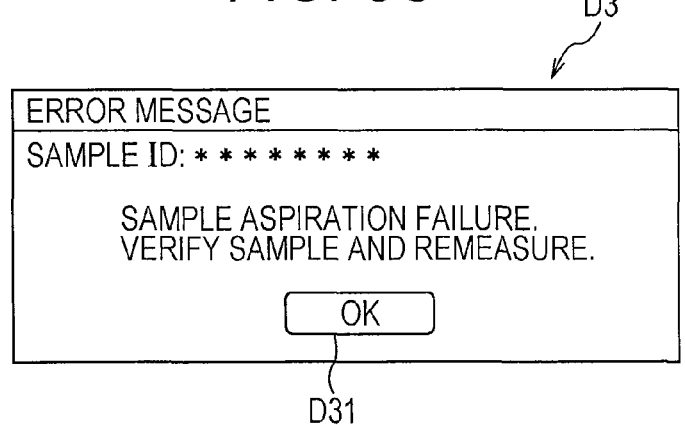

FIGS. 8A through 8C show examples of screens displayed on the display unit 420 of the information processing device 4 in the error process of S113.

When it is determined via the determination method of FIG. 6D that the sample filter 201c is blocked, the error dialog D1 shown in FIG. 8A is shown on the display unit 420 of the information processing device 4. In this case the error message D1 includes both a message indicating that the sample filter 201c is blocked and a message prompting the washing of the sample filter 201c to eliminate the blockage. The error dialog D1 also includes a wash button D11 to start washing to remove the blockage, and a skip button D12 to skip washing to remove the blockage.

When the wash button D11 is pressed in the error dialog D1, the CPU 401 executes the washing operation to remove the blockage of the sample filter 201c. Specifically, the aspirating pipette 201a is moved to the washing tank 201g, and the flow of the washing liquid from the washing liquid container 201f is reversed within the aspirating unit. This procedure removes foreign substances accumulated on the sample filter 201c, thus eliminating the blockage of the sample filter 201c. When the washing operation is completed, the CPU 401 stops the display of the error dialog D1 and the process advances to S112 of FIG. 7. In S112, the flow of the washing liquid from the washing liquid container 201f is again reversed to remove foreign substances accumulated on the sample filter 201c. When the skip button D12 is pressed in the error dialog D1, the CPU 401 stops the display of the error dialog D1 and the process advances to S112 of FIG. 7.

When it is determined that there is no sample in the sample container T via the determination method of FIG. 6D, an error dialog D2 of FIG. 8B is shown on the display unit 420 of the information processing device 4. In this case the error dialog D2 includes a message indicating there is no sample in the sample container T. The error dialog D2 also includes an OK button D21 to advance the process. When the OK button D21 is pressed in the error dialog D2, the CPU 401 stops the display of the error dialog D2 and advances the process to S112 of FIG. 7.

When it is determined that the sample aspirating operation is improper for some reason via the determination method of FIG. 6D, an error dialog D3 shown in FIG. 8C is shown on the display unit 420 of the information processing device 4. In this case the error dialog D3 includes a message indicating sample was not properly aspirated. The error dialog D3 also includes an OK button D31 to advance the process. When the OK button D31 is pressed in the error dialog D3, the CPU 401 stops the display of the error dialog D3 and advances the process to S112 of FIG. 7.

When the flow path washing process of S112 is completed, the processing related to the sample of this sample container T ends. The CPU 401 then returns the process to S101, and waits the arrival of the next sample container T containing a sample to be measured at the aspirating position.

According to the present embodiment, the error detection in the sample aspirating operation is performed based on the combination of detection results of the liquid sensing unit 201d performed during the first aspiration operation, and the detection results of the liquid sensing unit 201d during the second aspirating operation. This allows broad detection of error in the aspirating operations including blockage of the sample filter 201c, no sample in the sample container T, or improper aspiration of sample for some reason.

According to the present embodiment, errors in the aspirating operations can be appropriately managed by detecting errors of the sample filter 201c which is susceptible to failure in normal usage.

According to the present embodiment, when an error is determined in the aspirating operation, an error message corresponding to the type of error in the aspirating operation is display as shown in FIGS. 8D and 8E. The operator is accordingly made aware of the error in the sample aspirating operation and can take appropriate action.

Also according to the present embodiment, when it is determined that the sample filter 201c is blocked, both a normal washing operation and an aspirating unit washing operation to unblock the obstruction are performed. The blockage of the sample filter 201c is therefore cleared and subsequent processing operations advance smoothly.

In the present embodiment, the amount of aspirated sample can be controlled by aspirating air in the second aspirating operation. The amount of sample passing through the sample filter 201c is reduced and blockage of the sample filter 201c thereby suppressed because the amount of sample aspirated is controlled in this manner.

Although described by way of the above embodiment, the present invention is not limited to this embodiment and may be variously modified.

First Modification

For example, although the amount of ample is measured by the sampling valve 201h in the above embodiment, the present invention also may be applied to urine analyzers which do not have sampling valves.

Figure 9:
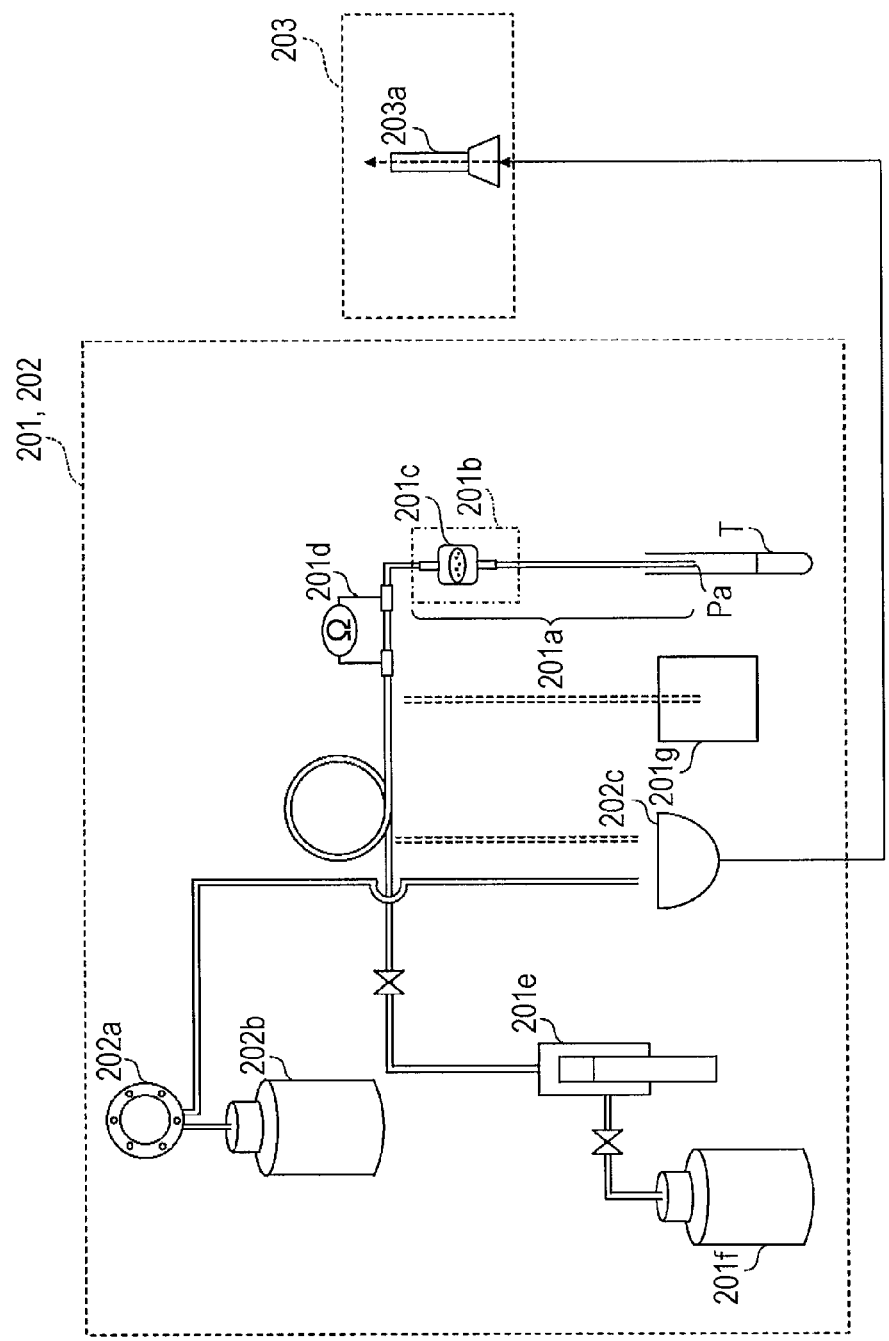
FIG. 9 briefly shows the structures of the sample distributing unit and the sample preparing unit of a first modification.

FIG. 9 briefly shows the structures of the sample distributing unit and the sample preparing unit of a first modification.

Compared to the above embodiment, the sample distributing unit 201 of the first modification omits the sampling valve 201h. The sample distributing unit 201 moves the aspirating pipette 201a containing the aspirated sample to the reaction chamber 202c by a predetermined drive mechanism (not shown in the drawing), and discharges the sample from the aspirating pipette 201a to the reaction chamber 202c.

FIGS. 10A through 10D schematically show the normal sample liquid aspirating operation of the first modification.

Figure 10A:
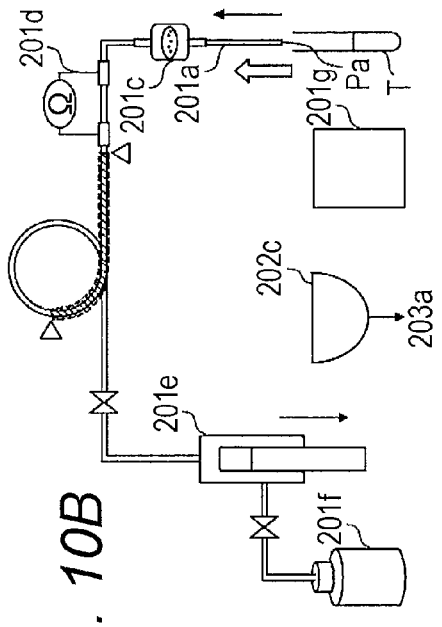
FIGS. 10A-10D schematically show the normal sample liquid aspirating operation.
Figure 10B:
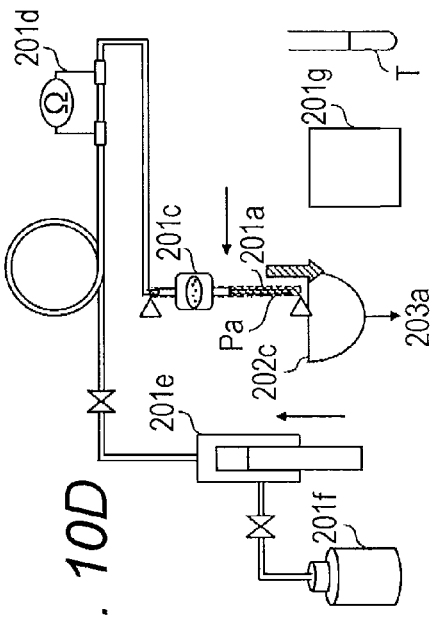

In the first modification, the first aspirating operation (sample aspiration) is performed with the aspirating pipette 201a in the lowered condition as shown in FIG. 10A similar to the above embodiment. The second aspirating operation (air aspiration) is thereafter performed with the aspirating pipette 201a in the raised condition as shown in FIG. 10B.

Figure 10C:
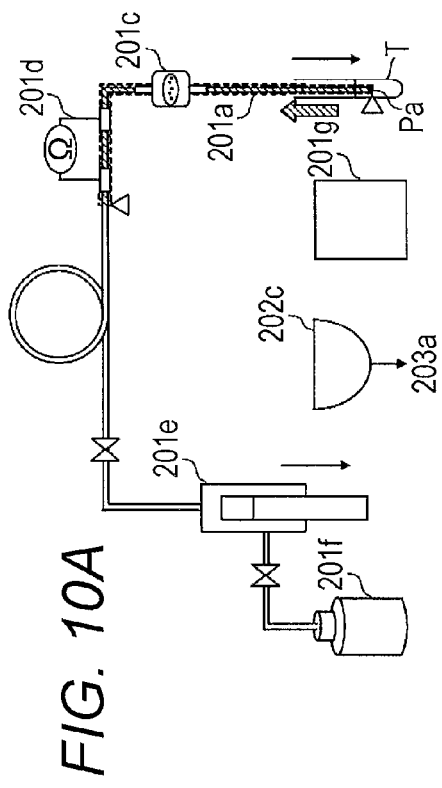
Figure 10D:
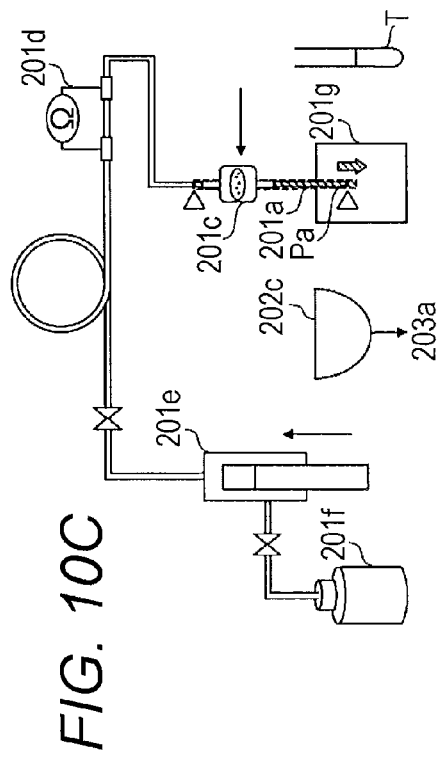

As shown in FIG. 10C, the aspirating pipette 201a is moved to the washing tank 201g by a predetermined drive mechanism (not shown in the drawing), and discharges part of the aspirated sample. Thereafter, the aspirating pipette 201a is moved to the reaction chamber 202c by a predetermined drive mechanism (not shown in the drawing), and discharges the aspirated sample into the reaction chamber 202c as shown in FIG. 10D. Note that since a mechanism is not provided to measure the amount of sample in the present modification, only the amount of sample required for the measurement process is aspirated given consideration of the amount of sample to be discharged into the washing tank 201g prior to the measurement process.

FIG. 11A schematically shows the condition of the flow path peripheral to the liquid sensing unit 201d during the normal sample liquid aspirating operation of the first modification. As shown in the drawing, part of the sample is discharged into the washing tank 201g after the second aspirating operation in the first modification.

FIG. 11B is a flow chart showing the control during the measurement operation of the first modification. The flow chart of FIG. 11B is a partial modification of the flow chart of FIG. 7 in that S121 is added.

Referring to FIG. 11B, when the aspirating process is determined to be normal (S110: YES), the CPU 401 moves the aspirating pipette 201a to the washing tank 201g via a predetermined drive mechanism, and part of the sample is discharged into the washing tank 201g (S121). The CPU 401 then discharges the remaining sample into the reaction chamber 202c, dispenses reagent to the reaction chamber 202c, and performs the measuring process (S111). When the measuring process is completed, the CPU 401 washes the flow path (S112).

When an error is determined in the aspirating operation (S110: NO), the CPU 401 executes an error process identical to the above embodiment (S113). In this case an error message corresponding to the error is displayed on the display unit 420 of the information processing device 4. Operations ( ) wash flow path, partial discharge of sample and the like) corresponding to instructions from the user in response to the message are then executed.

According to the configuration of the first modification, part of the sample is discharged to the washing tank 201g before the sample measuring process. In this way the flow of the sample is reversed in the aspirating unit, thereby removing foreign substances accumulated on the sample filter 201c and improving any blockage of the aspirating unit. Subsequent aspirating operations thus can be performed appropriately.

Second Modification

In the above modification whether an error has occurred in the aspirating operation is determined by combining the detection results on the presence or absence of sample in the second aspirating operation. However, the number of aspirating operations is not limited to two inasmuch as the determination of whether an error occurs in the aspirating operation can be accomplished by combining detection results on the presence or absence of sample in, for example, three aspirating operations.

Figure 12A:
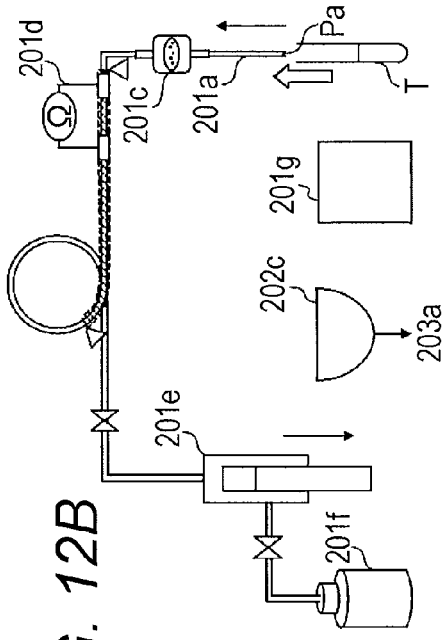
FIGS. 12A-12C schematically show the normal sample liquid aspirating operation of a second modification.
Figure 12B:
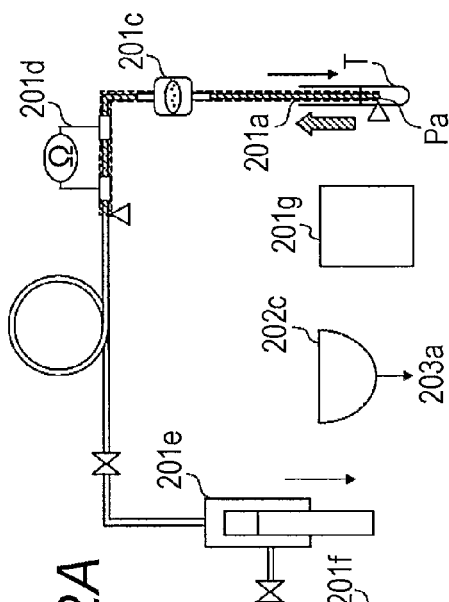
Figure 12C:
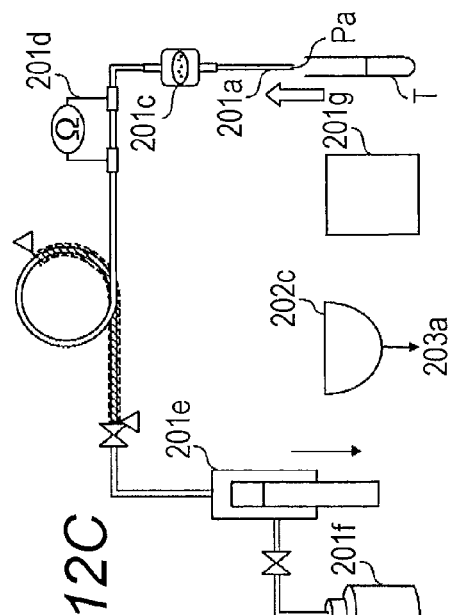

FIGS. 12A through 12C schematically show the normal sample liquid aspirating operation of the second modification. FIG. 13A schematically shows the condition of the flow path peripheral to the liquid sensing unit 201d during the normal sample liquid aspirating operation of the second modification. FIG. 13B shows an example of the determination method of the sample aspirating operation of the second modification. Note that the second modification applies the present invention to a urine analyzer which does not use a sampling valve similar to the first modification.

Referring to FIG. 12A, during sample aspiration the aspirating pipette 201a is first lowered so that the aspiration port Pa of the aspirating pipette 201a is submerged in the sample liquid held in the sample container T. In this condition a negative pressure is induced by the syringe pump 201e to aspirate the sample. The sample is thereby moved through the sampling valve 201c to the downstream side of the aspirating unit. In the first aspirating operation, the sample is positioned so that the front end of the sampling liquid is at a position exceeding the position of the electrodes of the liquid sensing unit 201d. Thus, the condition shown in the second drawing from the left of FIG. 13A is attained. In this condition the sample liquid is detected by the liquid sensing unit 201d because the sample is interposed between the electrodes of the sample sensing unit 201d.

As shown in FIG. 12B, the aspirating pipette 201a is then raised so that the aspiration port Pa is separated from the surface of the sample liquid held in the sample container T. In this condition a negative pressure is induced by the syringe pump 201e to aspirate air. The sample previously aspirated in the first aspirating operation is thereby moved to the downstream side of the aspirating unit. In the second aspirating operation, the sample is positioned so that the back end of the sampling liquid is at a position exceeding the position of the electrodes of the liquid sensing unit 201d. Thus, the condition shown in the center part of FIG. 13A is achieved. In this condition the sample liquid is detected by the liquid sensing unit 201d because the sample is interposed between the electrodes of the sample sensing unit 201d.

Referring to FIG. 12C, a negative pressure is thereafter induced by the syringe pump 201e to aspirate air while the aspirating pipette 201a is maintained in the raised condition. The sample previously aspirated in the first aspirating operation is thereby moved to the downstream side of the aspirating unit. In the third aspirating operation, the sample is positioned so that the back end of the sampling liquid is at a position exceeding the position of the electrodes of the liquid sensing unit 201d. Thus, the condition shown in the right part of FIG. 13A is achieved. In this condition the sample liquid is not detected by the liquid sensing unit 201d because air is interposed between the electrodes of the sample sensing unit 201d.

After part of the sample is discharged to the washing tank 201g, the sample is then discharged into the reaction chamber 202c similar to the first modification.

Note that when the aspirating operation is performed normally in the second modification, the amounts of sample and air and the length of the flow path configuring the flow path device are adjusted so that the sample is detected in the first aspirating operation (sample aspiration) and in the second aspirating operation (air aspiration), and sample is not detected in the third aspirating operation (air aspiration).

Whether an error occurs in the aspirating operations can be determined via this configuration of the flow path device based on the detection results indicating the presence and absence of sample during the three aspirating operations. As shown in FIG. 13B, in the second modification the types of more errors of the aspirating operation can be determined based on the combination of several detection results than in the above embodiment.

When sample in not detected in any of the first through third aspirating operations, it is determined that there is no sample in the sample container T. When sample is detected in all of the first through third aspirating operations, it is determined that the sample filter 201c is blocked. When sample is detected in the first aspirating operation but sample is not detected in the second and third aspirating operations, it is determined that insufficient sample amount less than a standard amount is present in the sample container T. When other detection results are combined, it is possible to determine an inappropriate condition for some reason in the sample aspirating operation.

According to the second modification, the determination of insufficient sample can be made unlike the above embodiment. When the amount of sample held in the sample container T is less than a standard amount in the above embodiment, sample can be detected in the first aspirating operation but sample cannot be detected in the second aspirating operation. The detection result is identical to that of a normal aspirating operation. When sample is insufficient as shown in FIG. 13B in the second modification, the sample is not detected in the second aspirating operation and the detection result differs from that of a normal aspirating operation. Hence, the determination discriminates between insufficient sample and a normal aspirating operation.

FIG. 14 is a flow chart showing the control during the measurement operation of the second modification. In the flow chart of FIG. 14, the steps of S106 through S109 of FIG. 11B are changes to S131 through S137. That is, the aspirating operation to aspirate air is performed twice.

When the first aspirating operation (sample aspiration) is completed by S102 through S105, the CPU 401 raises the aspirating pipette 201a so that the aspiration port Pa is separated from the surface of the sample (S131), and the executes the second aspirating operation (air Aspiration) of the measuring device 2 (S132). The CPU 401 then determines whether sample was detected by the liquid sensing unit 201d (S133). When the sample has been detected by the liquid sensing unit 201d (S133: YES), the CPU 401 stores the flag information indicating that sample has been detected in the second aspirating operation in the RAM 403 (S134). When sample is not detected by the liquid sensing unit 201d (S133: NO), the CPU 401 advances the process to S135. This completes the second aspirating operation.

The CPU 401 then executes the third aspirating operation (air aspiration) of the measuring device 2 (S135) while the aspiration port Pa of the aspirating pipette 201a is separated from the surface of the sample. The CPU 401 then determines whether sample was detected by the liquid sensing unit 201d (S136). When the sample has been detected by the liquid sensing unit 201d (S136: YES), the CPU 401 stores the flag information indicating that sample has been detected in the third aspirating operation in the RAM 403 (S137). When sample is not detected by the liquid sensing unit 201d (S136: NO), the CPU 401 advances the process to S110. This completes the third aspirating operation.

The CPU 401 then references the flag information stored in the RAM 403, and determines whether the sample aspirating operations were normal based on the detection results on the presence or absence of the sample in the first through third aspirating operations (S110). This determination is made based on the determination method shown in FIG. 13B.

Specifically, the sample operations are determined to be normal when sample is detected in the first aspirating operation, and sample is detected in the second aspirating operation, and sample is not detected in the third aspirating operation. When sample is detected in the first aspirating operation but sample is not detected in the second and third aspirating operations, it is determined that the amount of sample held in the sample container T is insufficient. When sample in not detected in any of the first through third aspirating operations, it is determined that there is no sample in the sample container T. When sample is detected in all of the first through third aspirating operations, it is determined that the sample filter 201c is blocked. In other cases it is determined that sample cannot be appropriately aspirated for some reason.

In S113 of FIG. 14, an error dialog corresponding to the error is displayed and operations are performed according to the instructions input in the error dialog similar to the above embodiment. In the second modification, insufficient sample can be determined unlike the above embodiment which cannot.

Figure 15A:
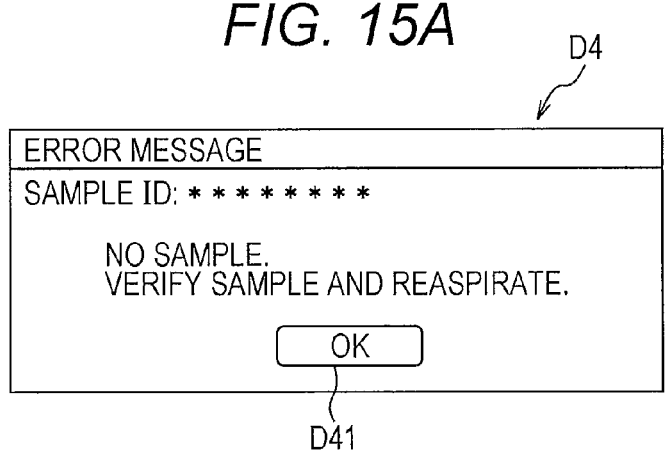
FIGS. 15A-15C are flow charts showing the error processing of the second and third modifications, and shows examples of screens displayed on the display unit of the information processing apparatus during error processing.

FIG. 15A shows examples of the error message screen in the case of insufficient sample.

Referring to FIG. 15A, the error dialog D4 includes a message indicating the sample liquid is insufficient. The error dialog D4 also includes an OK button D41 to advance the process to return to the normal measuring process. When the OK button D41 is pressed in the error dialog D4, the CPU 401 stops the display of the error dialog D4 and advances the process to S112 of FIG. 14. The washing operation of the flow path is performed (S112), and the process returns to the measurement standby condition for the next sample (S101).

In the second modification, the normal aspirating operation and sample insufficiency can be appropriately differentiated as described above. Therefore, the presence or absence of an error in the aspirating operation can be determined with greater precision in the second modification than in the above embodiment.

Note that in addition to the example shown in FIG. 13B, the method of determining errors in the aspirating operation may be suitably and variously modified according to the likelihood of error in the aspirating operation. Although the presence or absence of error in the aspirating operation is determined based on the detection results concerning the presence or absence of sample liquid in three aspirating operations in the case of the second modification, the presence or absence of error in the aspirating operations also may be determined based on detection results concerning the presence or absence of sample liquid in four or more aspirating operations.

Third Modification

When a blockage in the sample filter 201c is detected in the above embodiment, the dialog box D1 shown in FIG. 8A is displayed, and the decision as to whether to execute the washing process of the sample filter 201c is left to the discretion of the operator. However, the present invention is not limited to this method inasmuch as the process of washing the sample filter 201c also may be executed automatically when a blockage in the sample filter 201c is detected.

Figure 15B:
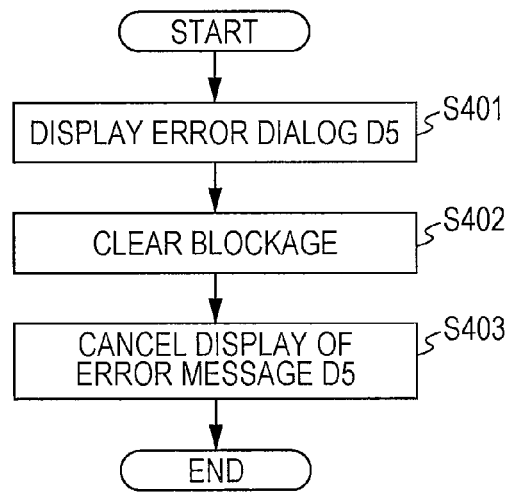

FIG. 15B is a flow chart showing the process in this case. This process is executed when the error concerns a blockage of the sample filter 201c in S113 of FIG. 7 or FIG. 14.

Figure 15C:
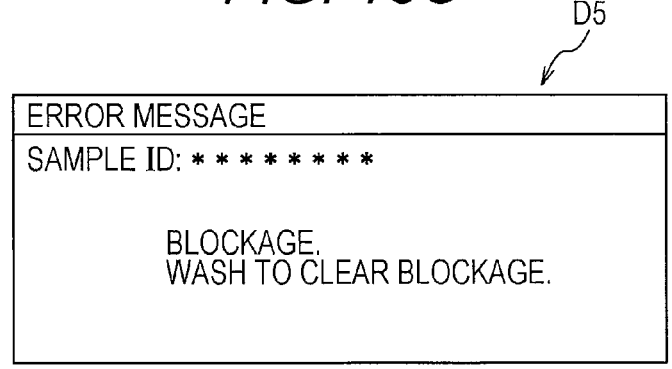

Referring to FIG. 15B, when the sample filter 201c becomes blocked, the CPU 401 shows the error dialog D5 shown in FIG. 15C on the display unit 420 of the information processing device 4 (S401). In this case the error message D5 includes both a message indicating that the sample filter 201c is blocked and a message indicating that the washing of the sample filter 201c was underway to eliminate the blockage.

The CPU 401 then automatically executes the washing operation to remove the blockage of the sample filter 201c (S402). Specifically, the aspirating pipette 201a is moved to the washing tank 201g, and the flow of the washing liquid from the washing liquid container 201f is reversed within the aspirating unit. This procedure removes foreign substances accumulated on the sample filter 201c, thus eliminating the blockage of the sample filter 201c. When the washing operation is completed, the CPU 401 stops the display of the error dialog D5 (S403) and the process advances to S112 of FIG. 7.

When configured as the third modification, the measuring device 2 can smoothly return to a condition capable of measuring the next sample because the washing operation to remove the blockage is executed automatically without waiting for the decision of the operator.

Similarly, the OK button may be omitted and the measuring device 2 also can automatically return to the condition capable of measuring the next sample in the case of the aspirating operation error examples shown in FIGS. 8B, 8C, and 15A.

Furthermore, the operator also may be alerted to the aspirating operation error by other means such as audio or the like instead of displaying the error dialog D1 through D5 on the displayed screen.

Fourth Modification

In the above embodiment, the determination whether sample aspiration was normal is made in each aspiration operation with a single timing and reference to detection results on the presence or absence of sample liquid by the liquid sensing unit 201d. However, in this case the negative pressure in the flow path may continue even after the aspiration operation is completed, thereby moving the sample and aspirated air through the flow path. Therefore, in methods for detecting the presence or absence of a sample using a single timing, it is possible that the detection of the presence or absence of sample may not be appropriately performed in each aspirating operation. When bubbles or a small amount of sample is aspirated, by chance sample liquid may be deposited between the electrodes of the liquid sensing unit 201d. In this case sample detection by the liquid sensing unit 201d may fail even though the sample aspirating operation is performed properly.

In the fourth modification, whether the sample aspiration was performed properly is determined by referencing the detection results of the presence or absence of sample liquid with two different timings in each aspirating operation in order to determine the presence or absence of error in the aspirating operation with greater accuracy.

FIGS. 16A and 16B are flow charts showing the control process during the measuring operation in the fourth modification. The flow charts of FIGS. 16A and 16B change part of the flow chart of FIG. 7 inasmuch as the process of S104 of FIG. 7 is replaced by S151 and S152, and the process of S108 of FIG. 7 is replaced by S161 and S162, respectively.

Referring to FIG. 16A, when the first aspirating operation (sample aspiration) is performed (S102, S103), the CPU 401 determines whether the sample liquid is detected by the liquid sensing unit 201d with a first timing after the aspiration operation (S151). When the sample liquid is detected (S151: YES), the CPU 401 then determines whether sample liquid is detected by the liquid sensing unit 201d with a second timing after a predetermined time has elapsed following the first timing (S152). Note that the interval between the first timing and second timing may be set very short.

When the sample is detected with the first timing (S151: YES) and sample is detected with the second timing (S152: YES), the CPU 401 stores the flag information indicating sample was detected in the first aspirating operation in the RAM 403 (S105). When sample is not detected with the first timing (S151: NO) or the sample is not detected with the second timing (S152: NO), the CPU 401 advances the process to S106. This completes the first aspirating operation.

Flag information indicating that sample liquid is detected is set when both detection results concerning the presence or absence of sample indicate sample is present in both timings in the first aspirating operation. Therefore, even when by chance a bubble is interposed between the electrodes of the liquid sensing unit 201d in the first timing, the bubble is eliminated from between the electrodes in the subsequent second timing, thereby avoiding mistaking the bubble aspiration for the sample aspiration.

Referring to FIG. 16B, when the second aspirating operation (air aspiration) is performed (S106, S107), the CPU 401 determines whether the sample liquid is detected by the liquid sensing unit 201d with a third timing after the aspiration operation (S161). When the sample liquid is detected (S161: YES), the CPU 401 then determines whether sample liquid is detected by the liquid sensing unit 201*d* with a fourth timing after a predetermined time has elapsed following the third timing (S162). Note that the interval between the third timing and fourth timing may be set very short.

When the sample is detected with the third timing (S161: YES) and sample is detected with the fourth timing (S162: YES), the CPU 401 stores the flag information indicating sample was detected in the second aspirating operation in the RAM 403 (S109). When sample is not detected with the third timing (S161: NO) or the sample is not detected with the second timing (S162: NO), the CPU 401 advances the process to S110. This completes the second aspirating operation.

Air is considered to be present when at least one of the detection results concerning the presence or absence of sample liquid in the two timings indicates sample liquid absent in the second aspirating operation. Therefore, even when sample adhered to the inner wall of the flow path by chance is disposed between the electrodes of the liquid sensing unit 201*d* in the third timing, the sample liquid will have moved from between the electrodes in the subsequent fourth timing and it is properly determined that air is present at the detecting position of the liquid sensing unit 201*d*.

Note that in order to determine the presence or absence of errors of the aspirating operation with high accuracy, the time taken to determine the voltage fluctuation and distance between electrodes of the liquid sensing unit 201*d* may be increased. However, in this case the time for a single measurement is increased while reducing measurement efficiency. Alternatively, in the case of the fourth modification, the time required to measure a sample can be reduced and the presence or absence of errors in the aspirating operation can be determined with better accuracy because the presence or absence of air or sample is based on two detection results of the presence or absence of sample performed in a very short time interval. Note that detection results of the presence or absence of sample in three or more timings also may be referenced in each aspirating operation.

Other Modifications

Although urine is the measurement object in the examples of the above embodiment, blood or other bodily fluid also may be a measurement object. That is, the present invention also is applicable to sample analyzers for examining bodily fluids. In this case bodily fluids refer to body fluids in the body cavity. Specifically, cerebrospinal fluid (CSF: fluid filling the subarachnoid space and ventricle), pleural fluid (PE: fluid collected in the pleural cavity), ascites fluid (fluid collected in the peritoneal cavity), pericardial fluid (fluid collected in the pericardial space), joint fluid (fluid present in joints, synovial sac, tendon sheaths). Peritoneal dialysis (CAPD) dialysis fluid and intraperitoneal cleaning solution are included as a type of body fluid.

In the above embodiment, when sample is detected in all aspirating operations, the determination is that sample filter 201*c* is blocked. However, in addition to blockage of the sample filter 201*c*, contamination of the aspirating pipette 201*a* by a foreign substance, fluid leakage from the flow path, or pump blockage or other impairment of the aspirating unit may produce a similar detection result. Therefore, when sample is detected in all aspirating operations, there is a possibility of these errors occurring may be included in the error message, or a corresponding return operation may be performed.

The screen examples in the above embodiment and first through fourth modifications may be suitably modified depending on the type of aspiration operation error and type of return operation.

Although a syringe pump is used as a generating source for the negative pressure to aspirate sample in the above embodiment, various pumps may be used such a diaphragm pump. Although an aspiration line connects the aspirating pipette 201*a* and syringe pump 201*e* in the aspirating unit, the syringe pump 201*e* also may be directly connected to the aspirating pipette 201*a*.

Figure 17:
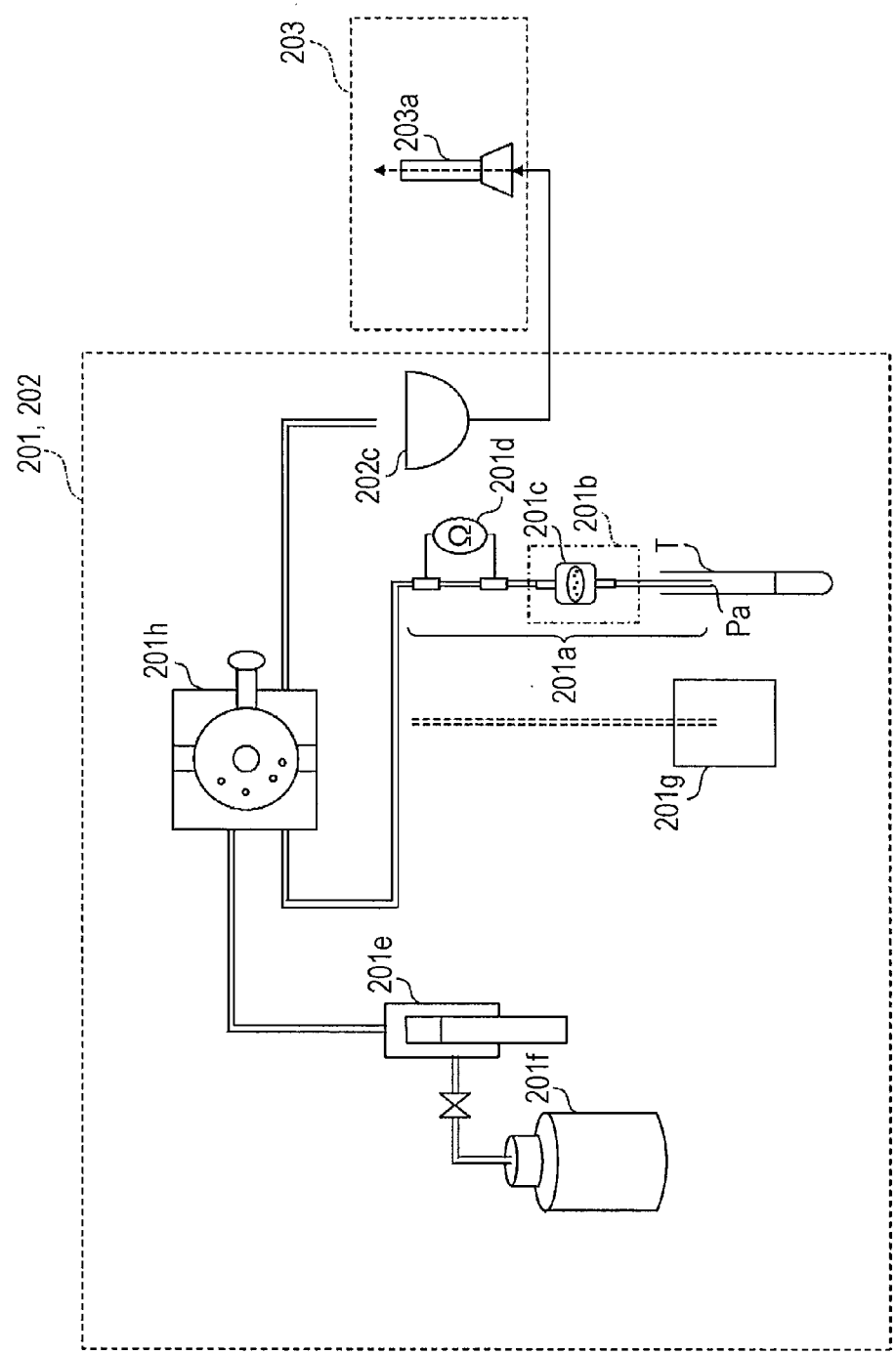
FIG. 17 briefly shows the structures of the sample distributing unit and the sample preparing unit of another modification.

Although the liquid sensing unit 201*d* is provided with an aspirating line to connect the aspirating pipette 201*a* and the syringe pump 201*e* in the above embodiment, the liquid sensing unit 201*d* may be in the aspirating pipette 201*a* as shown in FIG. 17. The disposition position of the liquid sensing unit 201*d* may be suitably changed to a predetermined position between the aspiration port Pa of the aspirating pipette 201*a* and the syringe pump 201*e*.

Although the sample container T is transported to the aspirating position (position directly below the aspirating pipette 201*a*) by the sample rack L in the above embodiment and the first through fourth modifications, the present invention may be applied to sample analyzers of the type which manually insert the sample container T in the aspirating pipette exposed to the outside of the apparatus. In this case the present invention can be effectively applied to such sample analyzers because errors can be readily introduced to the aspirating operation by a shaking hand and the like.

Note that the present invention is not limited to the above described embodiments and may be variously modified insofar as such modification are within the scope of the claims.

What is claimed is:

1. A sample processing apparatus, comprising:
   an aspirating member comprising a pump at a first side of the aspirating member, an aspiration port at a second side of the aspirating member, and an aspiration line between the pump and the aspiration port, the aspirating member configured to aspirate a sample from the aspiration port through the aspiration line;
   a sensor configured to sense a presence or absence of a liquid at a position of the aspiration line; and
   a controller programmed to execute operations, wherein the operations comprise:
   controlling the aspirating member to aspirate the sample during a first aspiration operation;
   controlling the aspirating member to aspirate air during a second aspiration operation after the first aspiration operation; and
   determining that an overall aspirating operation is in an error condition where the sensor fails to detect the presence of the liquid during the first aspiration operation and detects a presence or an absence of the liquid during the second aspiration operation.

2. The sample processing apparatus of claim 1, wherein the aspirating member further comprises an aspirating pipette on the second side; and the aspirating pipette aspirates the sample from a container through the aspiration port.

3. The sample processing apparatus of claim 2, wherein the controller elevates the aspirating pipette to position the aspiration port outside the sample when the aspirating member aspirates air.

4. The sample processing apparatus of claim 2, wherein the sensor is provided on the aspirating pipette.

5. The sample processing apparatus of claim 2, wherein the aspiration line connects the aspirating pipette and the pump, and the sensor is provided on the aspiration line.

6. The sample processing apparatus of claim 1, wherein the controller detects the presence of liquid via the sensor when the aspirating member aspirates sample, and detects an insufficient flow of sample in the aspirating member as the error condition when the sensor detects the presence of liquid at a predetermined position when the aspirating member aspirates air.

7. The sample processing apparatus of claim 6, wherein the controller detects the absence of liquid at a predetermined position via the sensor when the aspirating member aspirates sample, and detects an insufficient amount of sample for aspiration in the container as the error condition when the sensor detects the absence of liquid at a predetermined position when the aspirating member aspirates air.

8. The sample processing apparatus of claim 1, wherein the aspirating member further comprises a filter for removing foreign matter from the sample.

9. The sample processing apparatus of claim 1, wherein the controller controls the aspirating member to perform a third aspirating operation to aspirate air between the first aspirating operation and the second aspirating operation, and determines the aspirating operation is not in an error condition where the sensor detects the presence of the liquid during the third aspirating operation.

10. The sample processing apparatus of claim 1, wherein the controller performs an operation to flow the sample to the aspiration port through the aspiration line after the second aspiration operation but before execution of a sample processing operation.

11. The sample processing apparatus of claim 1, wherein the controller further performs an error notifying operation to notify the operation that an error has been detected.

12. The sample processing apparatus of claim 1, wherein the controller performs a restoring operation to correct an error where the controller determines the aspirating operation is an error condition.

13. An error detecting method for a sample processing apparatus, the method comprising:
  performing a first aspiration operation of aspirating the sample with an aspirating member, the aspirating member comprising a pump at a first side of the aspirating member, an aspiration port at a second side of the aspirating member and an aspiration line between the pump and the aspiration port which;
  performing a second aspiration operation of aspirating air with the aspirating member after the first aspiration operation; and
  determining that an overall aspirating operation is in an error condition where a sensor provided at the aspiration line detects an absence of a liquid during the first aspiration operation and a presence or an absence of a liquid during the second aspiration operation.

14. The error detecting method of claim 13, wherein the aspirating member further comprises an aspirating pipette, and the aspirating pipette is elevated to position the pipette outside the sample when the aspirating member aspirates air.

15. The error detecting method of claim 13, wherein the sensor detects the presence of liquid when the aspirating member aspirates sample, and detects an insufficient flow of sample in the aspirating member as the error condition when the sensor detects the presence of liquid at a predetermined position when the aspirating member aspirates air.

16. The error detecting method of claim 15, wherein the sensor detects the absence of liquid at a predetermined position when the aspirating member aspirates sample, and the sensor detects an insufficient amount of sample for aspiration in the container as the error condition when the sensor detects the absence of liquid at a predetermined position when the aspirating member aspirates air.

17. The error detecting method of claim 13, further comprising:
  performing a third aspirating operation of aspirating air between the first aspirating operation and the second aspirating operation, and
  determining the aspirating operation is not in an error condition where the sensor detects the presence of the liquid during the third aspirating operation.

18. The error detecting method of claim 13, further comprising:
  flowing the sample to the aspiration port after the second aspiration operation but before the execution of a sample processing operation.

19. The error detecting method of claim 13, further comprising notifying an operator that an error has been detected.

20. The error detecting method of claim 13, further comprising correcting an error when the error is detected.

* * * * *